(12) United States Patent
Geisel

(10) Patent No.: US 6,906,530 B2
(45) Date of Patent: Jun. 14, 2005

(54) APPARATUS AND METHOD TO DETECT MOISTURE

(75) Inventor: Donald J. Geisel, Clifton Park, NY (US)

(73) Assignees: D.J. Geisel Technology, Inc., Clifton Park, NJ (US); Donald J. Geisel & Assoc., Inc., Clifton Park, NY (US)

( * ) Notice: Subject to any disclaimer, the term of this patent is extended or adjusted under 35 U.S.C. 154(b) by 156 days.

(21) Appl. No.: 10/439,556

(22) Filed: May 17, 2003

(65) Prior Publication Data

US 2003/0222662 A1 Dec. 4, 2003

Related U.S. Application Data

(60) Provisional application No. 60/384,500, filed on May 30, 2002.

(51) Int. Cl.[7] .............................................. G01R 27/26
(52) U.S. Cl. ........................ 324/664; 324/545; 324/683; 324/640; 73/73
(58) Field of Search ................................ 324/664, 545, 324/551, 772, 663, 683, 640; 73/73

(56) References Cited

U.S. PATENT DOCUMENTS

| | | | |
|---|---|---|---|
| 3,694,742 A | * | 9/1972 | Bergmanis et al. ......... 324/663 |
| 3,778,707 A | * | 12/1973 | Vogel .......................... 324/659 |
| 4,224,565 A | | 9/1980 | Sosniak et al. |
| 4,580,233 A | * | 4/1986 | Parker et al. ................... 73/73 |
| 4,626,774 A | * | 12/1986 | Regtien ....................... 324/683 |
| 4,683,418 A | | 7/1987 | Wagner et al. |
| 4,972,154 A | * | 11/1990 | Bechtel et al. .............. 324/663 |
| 4,991,915 A | * | 2/1991 | Thompson et al. ......... 324/640 |
| 5,546,008 A | * | 8/1996 | Sminchak et al. .......... 324/690 |
| 5,671,633 A | | 9/1997 | Wagner |
| 6,051,981 A | * | 4/2000 | Gershenfeld et al. ....... 324/663 |
| 6,114,863 A | * | 9/2000 | Krahn et al. ................. 324/664 |

* cited by examiner

Primary Examiner—Anjan K. Deb
(74) Attorney, Agent, or Firm—Schmeiser, Olsen & Watts

(57) ABSTRACT

A method and apparatus for detecting moisture. An oscillatory electrical signal $S_1$ generated by an oscillator is propagated into a body that includes an electrically insulative material. A signal due to $S_1$ emerges from the body as an oscillatory electrical signal $S_2$. The signals $S_1$ and $S_2$ differ in phase by $\Delta\phi$, wherein $\Delta\phi$ is indicative of moisture along a path traversed by $S_1$ within the insulative material, and wherein the conductance $\sigma$ of the insulative material is also indicative of the moisture along the path traversed by $S_1$ within the insulative material. $S_2$ is received at a sensing surface of a sensing part (e.g., probe, sensing antenna, etc.) and then transmitted to a moisture detecting device. The moisture detecting device determines from $S_1$ and $S_2$ a measure M of the moisture as a function of $\Delta\phi$ or as a function of $\sigma$.

70 Claims, 16 Drawing Sheets

APPARATUS AND METHOD TO DETECT MOISTURE

RELATED APPLICATION

The present invention claims priority to U.S. Provisional Application No. 60/384,500, filed on May 30, 2002, which is incorporated herein by reference in its entirety.

BACKGROUND OF THE INVENTION

1. Technical Field

The present invention relates to a method and apparatus for detecting moisture, and more particularly to a method and apparatus for detecting moisture in an electrically insulative portion of a body of mass.

2. Related Art

Large power generators can be water cooled by allowing the water to flow through the stator bars. Although this flowing water removes excessive heat, water leaks are common due to nearly a hundred stator bars in a mega-watt generator. The leaking water contaminates the electrical insulation, which surrounds the stator bar. These leaks can eventually cause a catastrophic failure. The ensuing failure could cause significant damage to the generator as well as lost revenue and customers may consequently experience loss of power or reduced power. Detection of moisture resulting from the leaking water at an early stage is therefore important for mitigating the effects of the leaking water. Some of the methods of detecting moisture in stator bars include visual inspection, gas leak testing, electrical hi-potting and capacitance mapping, each of which has disadvantages due to innacuracy and/or other difficulties. Thus there is a need for a more accurate and practical method and apparatus for detecting moisture at an early stage, wherein the moisture is due to water leaks in a power generator.

SUMMARY OF THE INVENTION

The present invention provides an apparatus for detecting moisture, comprising:

an oscillator for generating a first oscillatory electrical signal $S_1$;

means for propagating $S_1$ into a body such that a signal due to $S_1$ emerges from the body as a second oscillatory electrical signal $S_2$, wherein the body includes an electrically insulative material and an electrical conductor, and wherein $S_1$ and $S_2$ differ in phase by $\Delta\phi$ such that $\Delta\phi$ is indicative of moisture along a path traversed by $S_1$ within the insulative material;

a probe having an electrically conductive sensing surface adapted to be in physical contact with the body and to receive $S_2$, wherein the insulative material is disposed between the sensing surface and the electrical conductor so as to form a parallel plate capacitor; and a moisture detecting device adapted to determine from $S_1$ and $S_2$ a measure M of the moisture, said measure M being proportional to $\Delta\phi$.

The present invention provides a method for detecting moisture, comprising:

propagating a first oscillatory electrical signal $S_1$ into a body such that a signal due to $S_1$ emerges from the body as a second oscillatory electrical signal $S_2$, wherein the body includes an electrically insulative material and an electrical conductor, and wherein $S_1$ and $S_2$ differ in phase by $\Delta\phi$ such that $\Delta\phi$ is indicative of moisture along a path traversed by $S_1$ within the insulative material;

receiving $S_2$ by an electrically conductive sensing surface of a probe, wherein the sensing surface is in contact with the body, and wherein the insulative material is disposed between the sensing surface and the electrical conductor so as to form a parallel plate capacitor; and transmitting $S_2$ from the probe to a moisture detecting device that determines from $S_1$ and $S_2$ a measure M of the moisture, said measure M being proportional to $\Delta\phi$.

The present invention provides an apparatus for detecting moisture, comprising:

an oscillator for generating a first oscillatory electrical signal $S_1$;

means for propagating $S_1$ into a body such that a signal due to $S_1$ emerges from the body as a second oscillatory electrical signal $S_2$, wherein the body includes an electrically insulative material having a conductance $\sigma$, and wherein $\sigma$ is indicative of moisture along a path traversed by $S_1$ within the insulative material;

a sensing part having an electrically conductive sensing surface adapted to be in physical contact with the body and to receive $S_2$; and a moisture detecting device adapted to determine from $S_1$ and $S_2$ a measure M of the moisture, said measure M being a function of $\sigma$.

The present invention provides a method for detecting moisture, comprising:

propagating a first oscillatory electrical signal $S_1$ into a body such that a signal due to $S_1$ emerges from the body as a second oscillatory electrical signal $S_2$, wherein the body includes an electrically insulative material having a conductance $\sigma$, and wherein $\sigma$ is indicative of moisture along a path traversed by $S_1$ within the insulative material;

receiving $S_2$ by a sensing surface of a sensing part, wherein the sensing surface is in physical contact with the body; and transmitting $S_2$ from the sensing surface to a moisture detecting device that determines from $S_1$ and $S_2$ a measure M of the moisture, said measure M being a function of $\sigma$.

The present invention provides a more accurate and practical method and apparatus for detecting moisture at an early stage, wherein the moisture is due to water leaks in a power generator.

DETAILED DESCRIPTION OF THE INVENTION

Figure 1:
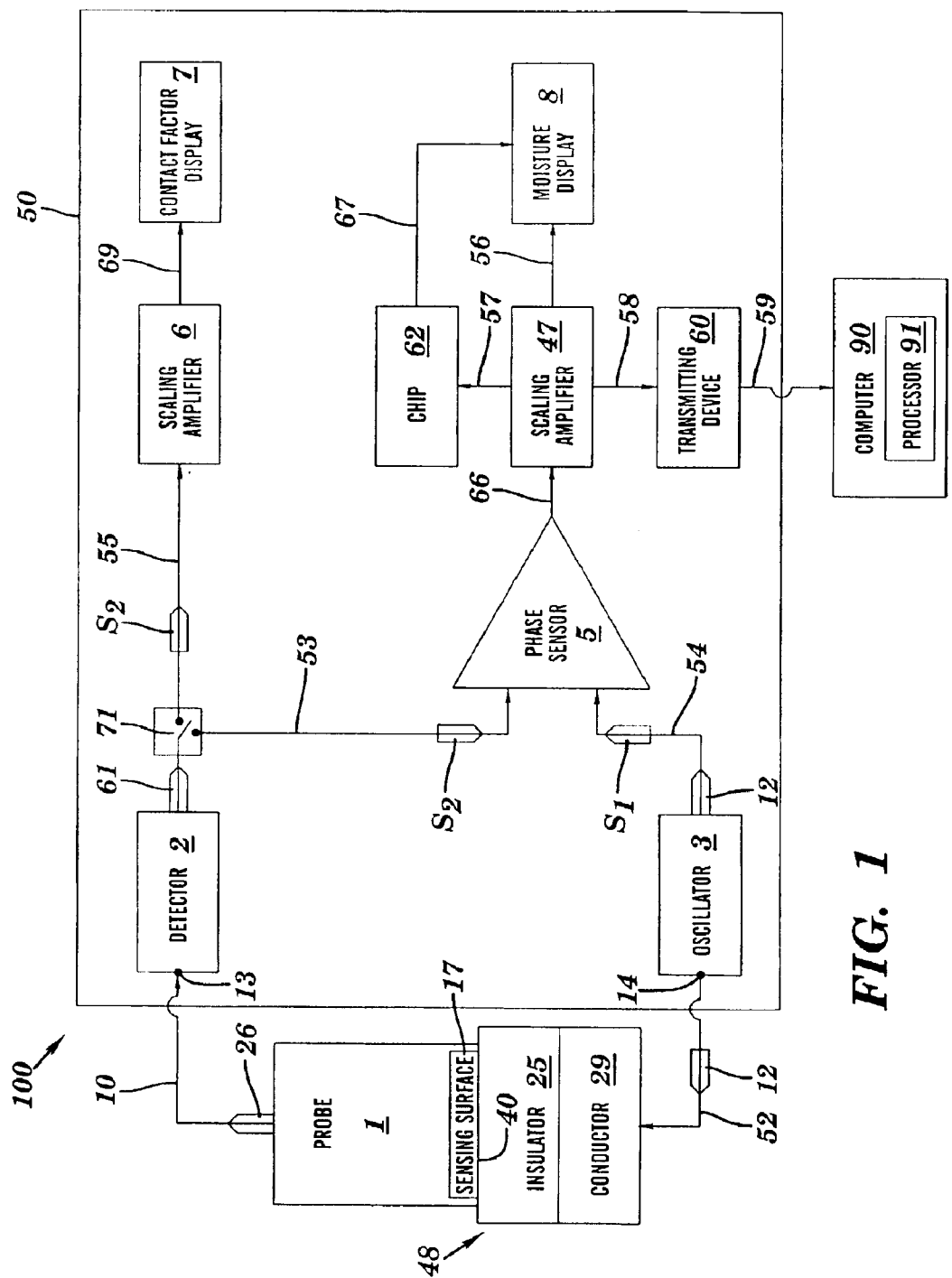
FIG. 1 is a block diagram of an apparatus for detecting moisture within insulation in a body through use of an oscillator signal detected by a probe, in accordance with embodiments of the present invention.

Dry and moist insulation has substantially different dielectric properties. The apparatus of the present invention can measure these properties and display both magnitude and phase of an electrical signal passing through the stator bar insulation. The phase of the signal is a good indication of moisture contamination. In electrical circuit theory, a pure insulator causes a 90 degree phase shift; i.e., the current leads the applied voltage by 90 degrees. A moist or lossy insulator will cause a several degree "off" 90 phase shift, such as 85 degrees. For simplicity, this disclosure will work with positive phases and phase shifts and will therefore assume, for a given insulation, that a signal has a reference phase of zero degrees when propagating through the given insulation in a purely dry state. Thus, a phase of zero degrees corresponds to a phase shift between the voltage and current of exactly 90 degrees. The same signal is phase shifted so as to acquire a phase of a few degrees positive when propagating through the given insulation in a moist state. Additionally, reference will be made to "signals" rather than voltage or current, with the understanding that the signal could consistently refer to voltage or current without altering the description of the embodiments of the present invention described herein.

A "purely dry" state is characterized by zero moisture content. In contrast, a "dry" state is characterized by ambient moisture content and a signal passing through dry insulation has a phase of about 2 degrees (i.e., a 2-degree differential from the purely dry 90 degree phase shift between the current and voltage). Moist insulation will cause a signal passing therethrough to acquire a phase shift significantly more than 2 degrees and upward to 20 degrees for high moisture content. With the present invention, the phase of a test signal after having passed through insulation is sensed by comparing the test signal with a reference signal generated by an oscillator. This comparison is made by using a moisture measuring device that receives the test signal from a probe, wherein the probe receives the test signal as the test signal emerges from the insulation. As a result of this comparison, a measure of the moisture content in the insulation is determined by the moisture measuring device and this measure may be subsequently displayed. The magnitude of the test signal may also be determined and displayed as a Contact Factor, which may be used by an operator to confirm that the probe is making good surface contact with the insulation surrounding the stator bar. The phase of the detected test signal will vary (e.g., typically increase) as moisture in the insulation increases. Hence, the phase of the detected test signal can be used as a moisture indicator, in accordance with the "Phase" embodiments of the present invention as discussed infra in conjunction with FIGS. 1–6.

Additionally, the electrical conductance $\sigma$ of the insulation, which is the reciprocal of the electrical resistance, varies (e.g., typically increases) as the moisture in the insulation increases. In the purely dry state, $\sigma=0$. Hence, a nonzero value of $\sigma$, or equivalently the finiteness of the electrical resistance of the insulation (as compared with the essentially infinite electrical resistance of dry insulation), may also be used as a moisture indicator, in accordance with the "Conductance" embodiments of the present invention as discussed infra in conjunction with FIGS. 7–16. Oscillator test frequencies of 1 Khz to 50 Mhz have been employed and may be used for the reference and test signals.

"Phase" Embodiments (FIGS. 1–6)

FIG. 1 is a block diagram of an apparatus 100, in accordance with embodiments of the present invention. The apparatus 100 includes an oscillator 3, a detector 2, a switch 71, a phase sensor 5, a scaling amplifier 6, a scaling amplifier 47, a moisture display 8, a semiconductor chip 62, and a transmitting device 60, all of which are enclosed within an enclosure 50. The apparatus 100 further includes a probe 1 which is electrically coupled to the detector 2 by an electrical connection 10 (e.g., cable). Additionally, the apparatus 100 may be powered by any voltage source (e.g., a battery pack). FIG. 1 also shows a body 48, which is generally a mass of matter, said body 48 comprising insulation 25 and an electrical conductor 29. An example of the body 48 is the power generator 27, discussed infra in conjunction with FIG. 2. The insulation 25 comprises an electrically insulative material. The apparatus 100 is adapted to detect and display, inter alia, moisture in the insulation 25 of the body 48.

The oscillator 3 generates an oscillatory signal (e.g., a sinusoidal signal) 12 which is also denoted symbolically as $S_1$. The signal 12 (i.e., $S_1$) is propagated along the electrical connection 52 (e.g., cable) from output node 14 of the oscillator 3 into the body 48; i.e into the conductor 29 and then through the insulation 25 to the exterior surface 40 of the insulation 25, said surface 40 also being the exterior surface of the body 48. The signal 12 may comprise a frequency from 1 Khz to 50 Mhz. The probe 1 is a "sensing part" that has an active electrically conductive sensing area/surface 17 for receiving the signal 12 from the surface 40 of the insulation 25. The signal 12 has been changed in its phase and magnitude by the moisture content within the insulation 25, as discussed infra in conjunction with FIG. 4, and will thus be denoted as the signal 26, or symbolically as $S_2$, as said signal emerges from the surface 40 and is received by the probe 1. After the signal 26 (i.e., $S_2$) is received by the probe 1, the signal 26 is detected and processed by the detector 2 after having been received at input node 13 of the detector 2. The detector 2 may include an amplifier to amplify the signal 26, because the signal 26 my be weak. The detector 2 may include a filter to remove unwanted frequencies from the signal 26. The signal 26 emerges from the detector 2 as the signal 61. However, the signal 61 is essentially the same signal as the signal 26 except for amplification and filtering by the detector 2, as discussed supra. The signal 26 emerges from the detector 2 as the signal 61. However, the signal 61 will be denoted by the same symbol $S_2$ that denotes the signal 26.

After emerging from the detector 2, the signal 61 passes through a switch 71 whose logic status determines whether the signal 61 is next propagated into electrical path 53 or electrical path 55. If the switch 71 is replaced by a single conductive node, then the signal 61 will propagate into both electrical path 53 and electrical path 55.

In electrical path 53, the signal 61 is denoted as $S_2$ and is propagated into the phase sensor 5. Additionally, the signal 12 generated by the oscillator 3, and denoted as $S_1$, is propagated along electrical path 53 into the phase sensor 5. The phase sensor 5 compares signals $S_1$ and $S_2$ to generate a phase-denoting signal that represents the phase difference $\Delta\phi$ (or a measure thereof) between signals $S_1$ and $S_2$. As stated supra, $\Delta\phi$ is caused by the presence of moisture in the insulation 25. Thus if the insulation 25 is purely dry then $\Delta\phi=0$. If the insulation 25 is dry to the extent of containing ambient moisture, but no more than ambient moisture, then $\Delta\phi\approx2$ degrees. If the insulation 25 has water content in excess of ambient moisture, then $\Delta\phi$ is greater than 2 degrees and may be as high as 20 degrees. It should be recalled that $\Delta\phi$ represents a deviation from the normal 90 degree phase shift between the voltage and the current that exists when the insulation 25 is purely dry and is thus characterized in the purely dry state by an impedance that includes pure capacitive reactance and infinite electrical resistance. Accordingly, $\Delta\phi$ is a function (e.g., an increasing function) of the moisture content along a path traversed by $S_1$ within the insulation 25.

The phase sensor 5 transmits the phase-denoting signal representing $\Delta\phi$ into a scaling amplifier 47 that converts or amplifies said phase-denoting signal into $\Delta\phi$ or a multiple thereof, to yield a measure M of the moisture (e.g., moisture density distribution, moisture weight, moisture volume, etc.) along a path traversed by $S_1$ within the insulative material of the insulation 25. Amplification of the phase-denoting signal by the scaling amplifier 47 serves to provide an adequate signal level for subsequent display by the moisture display 8. The measure M is passed along electrical path 56 to the moisture display 8 where M is displayed. The measure M received by the moisture display 8 from the scaling amplifier 47 is $\Delta\phi$ or a quantity that varies as a function of $\Delta\phi$ (e.g., a quantity proportional to $\Delta\phi$). However, if $\Delta\phi$ or a multiple thereof is passed to the semiconductor chip 62, such that the chip 62 is a compute element capable of performing computations, or more generally capable of executing an algorithm hard-coded therewithin, then the chip 62 may compute M to be generally be any desired function of $\Delta\phi$ (e.g., the average water density within the insulation 25, the weight or volume within the insulation 25, the electrical conductance or finite electrical resistance introduced by the moisture within the insulation 25, etc). Generally, M is a function of $\Delta\phi$ such as, inter alia, an increasing function of $\Delta\phi$. The chip 62 passes M along electrical path 67 to the moisture display 8 where M is displayed.

Alternatively, the measure M (e.g., $\Delta\phi$ or a multiple thereof) may be transmitted along electrical path 58 into a transmitting device 60, which transmits M over a communication path 59 to a remote computer system 90 (e.g., a desktop computer system, a laptop computer, a hand-held computer, etc.). The computer system 90 is considered to be a remote computer system if the computer system 90 is external to the enclosure 50. The communication path 59 may be a wired path or a wireless path, and may be any path that is known to a person of ordinary skill in the art (e.g., cable, telephone lines, an Internet path, an Intranet path, etc.). The computer system 90 includes a processor 91 which may execute an algorithm that computes any desired quantity relating to the measure M. Said function of the measure M may include: the average water density within the insulation 25, the weight or volume within the insulation 25, the finite electrical resistance introduced by the moisture within the insulation 25, etc. Additionally, the computer system 90 may store any such measured data received from the transmitting device 60, for later use such as, inter alia, graphically displaying at the computer system 90 how $\Delta\phi$ (or a function thereof) varies over a series of transmissions of such measured data to the computer system 90 over a period of time.

Figure 17:
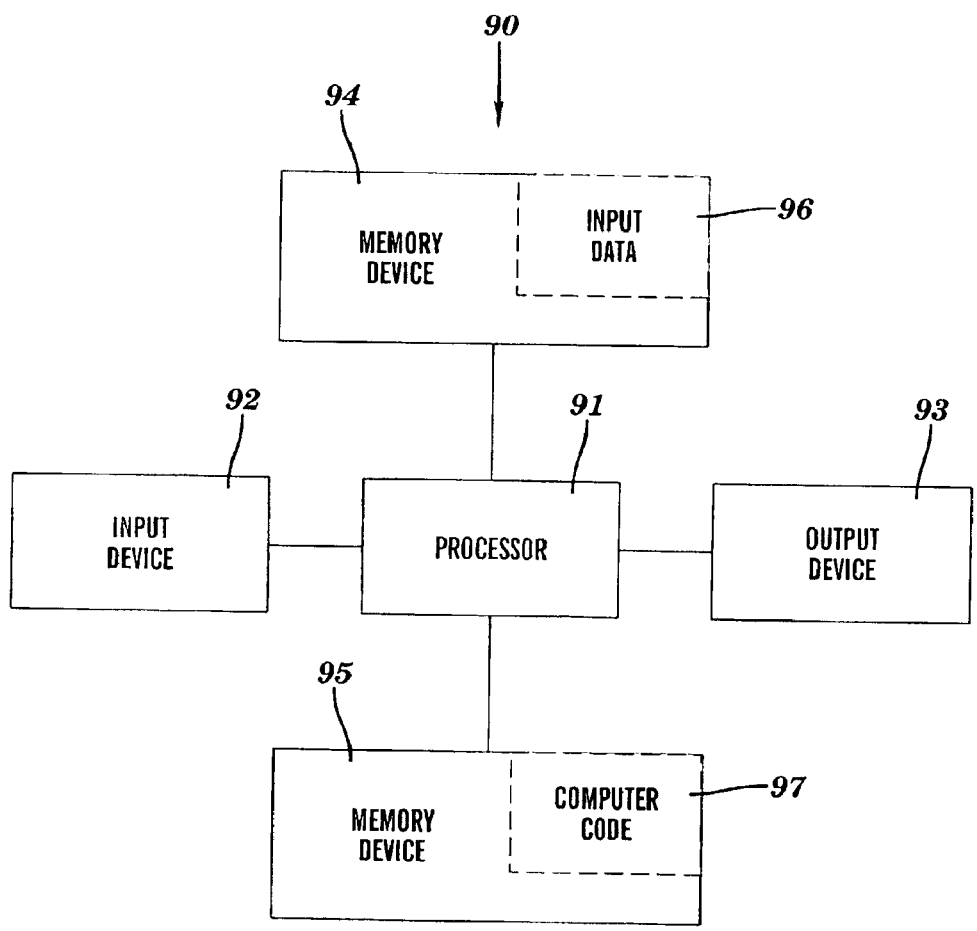
FIG. 17 illustrates a computer system, in accordance with embodiments of the present invention.

FIG. 17 illustrates the computer system 90, in accordance with embodiments of the present invention. The computer system 90 comprises the processor 91, an input device 92 coupled to the processor 91, an output device 93 coupled to the processor 91, and memory devices 94 and 95 each coupled to the processor 91. The input device 92 may be, inter alia, a keyboard, a mouse, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes an algorithm that computes any desired function of the measure M such as $\Delta\phi$, $V_{IN}$, etc., wherein $V_{IN}$ is the in-phase component of the signal $S_2$ as discussed infra in conjunction with FIG. 7. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices not shown in FIG. 17 may be used as a computer usable medium (or a computer readable medium or a program storage device) having a computer readable program code embodied therein and/or having other data stored therein, wherein the computer readable program code comprises the computer code 97. Generally, a computer program product (or, alternatively, an article of manufacture) of the computer system 90 may comprise said computer usable medium (or said program storage device). While FIG. 17 shows the computer system 90 as a particular configuration of hardware and software, any configuration of hardware and software, as would be known to a person of ordinary skill in the art, may be utilized for the purposes stated supra in conjunction with the particular computer system 90 of FIG. 17. For example, the memory devices 94 and 95 may be portions of a single memory device rather than separate memory devices.

In electrical path 55 of FIG. 1, the signal 61 is denoted as $S_2$ and is propagated into the scaling amplifier 6. The magnitude of $S_2$ is a measure of a contact factor CF of the degree of physical contact between the active sensing surface 17 of the probe 1 and the insulation 25 of the body 48. Amplification of $S_2$ by the scaling amplifier 6 serves to provide an adequate signal level for subsequent display by the contact factor display 7. The contact factor CF is passed along electrical path 69 from the scaling amplifier 6 to the contact factor display 7 where CF is displayed. The contact factor CF received by the contact factor display 7 from the scaling amplifier 6 is the magnitude of the signal $S_2$ or a multiple thereof. Note that CF may be passed to a semiconductor chip or transmitting device (not shown in FIG. 1) in a manner that is analogous to the transmission of M to the chip 62 or the transmitting device 60, such that any function of CF may be computed and displayed.

Figure 2:
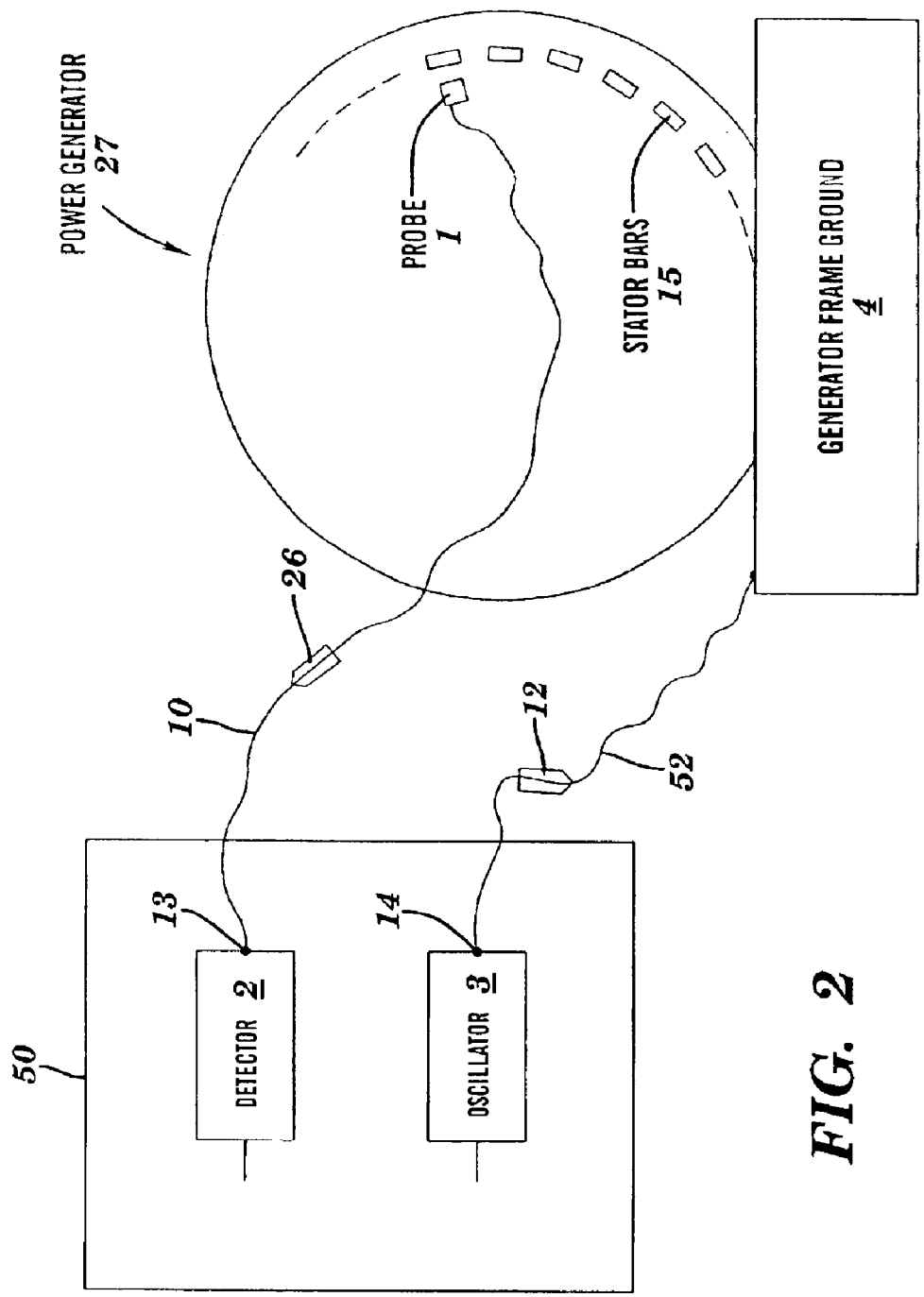
FIG. 2 depicts the apparatus of FIG. 1, wherein the body of FIG. 1 is represented by a power generator, in accordance with embodiments of the present invention.

FIG. 2 depicts the apparatus 100 of FIG. 1, wherein the body 48 of FIG. 1 is represented by a power generator 27 in FIG. 2, in accordance with embodiments of the present invention. The power generator 27 comprises stator bars 15 coupled to a generator frame ground 4. The stator bars 15 comprise or represent the electrical conductor 29 in FIG. 1. In FIG. 2, the output signal 12 (i.e., $S_1$) from the oscillator 3 (see FIG. 1) is propagated from output node 14 of the oscillator 3 to the generator frame ground 4 via the electrical connection 52. Since the stator bars 15 are also at ground potential, the oscillator signal $S_1$ appears on all stator bars 15 in the power generator 27. At radio frequencies, the oscillator signal $S_1$ will be coupled to any ungrounded stator bars by the sufficiently large capacitance between the stator bars and the generator frame ground 4, without a DC ground path existing between the copper center of the stator bars 15 and the generator frame ground 4. The probe 1 is positioned on the insulating surface 40 (shown infra in FIG. 3) of a stator bar 15. The signal 26 (i.e., $S_2$) received by the probe 1 is propagated to the input node 13 of the detector 2 via the electrical connection 10.

Figure 3:
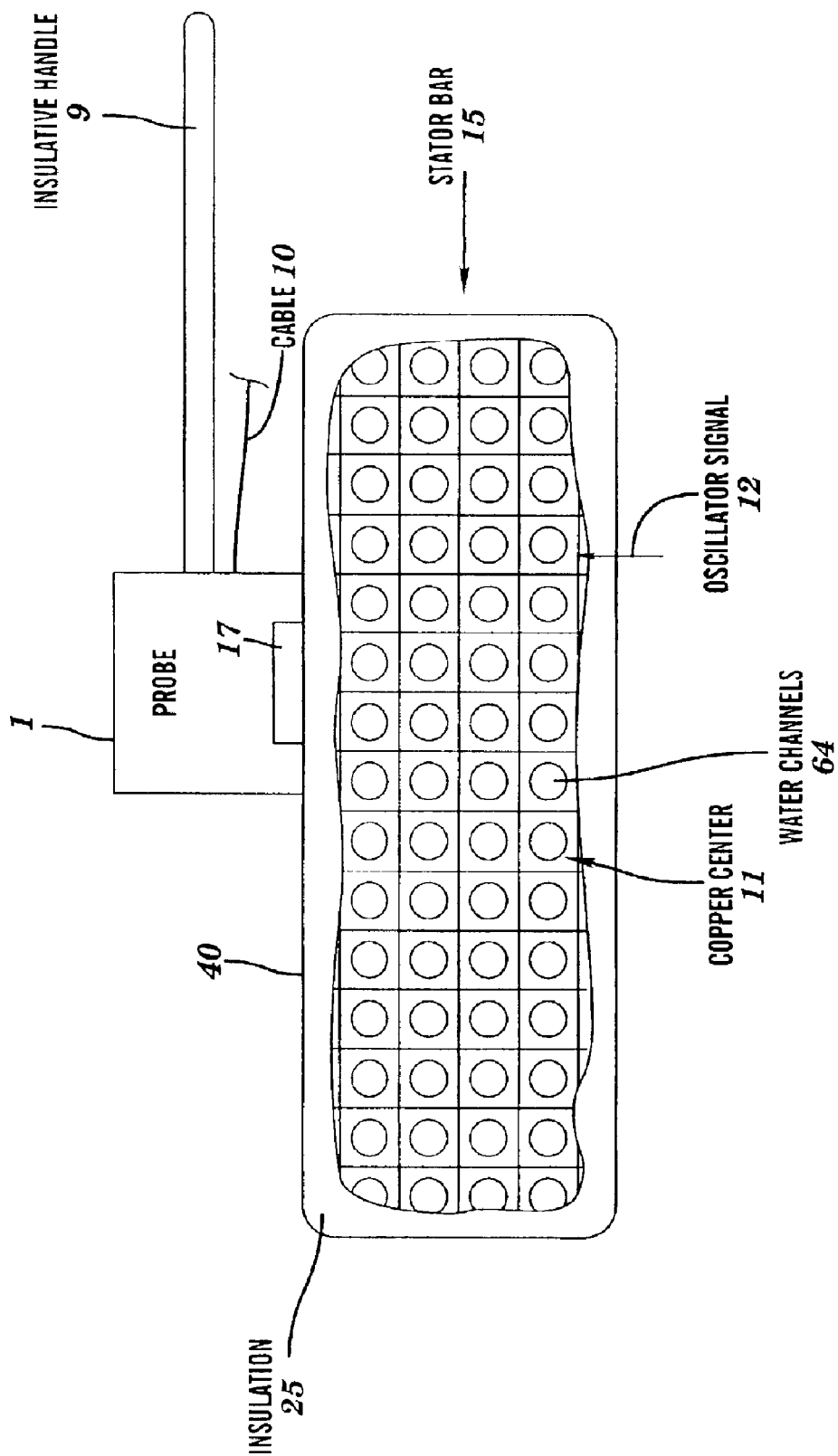
FIG. 3 depicts the oscillator signal appearing at the copper center of the stator bars of the power generator of FIG. 2, in accordance with embodiments of the present invention.

FIG. 3 depicts the oscillator signal 12 appearing at the copper center 11 of a stator bar 15, in accordance with embodiments of the present invention. The insulation 25 surrounds the copper center 11. The water channels 64 appearing within the copper center 11 provide a potential source of moisture in the insulation 25 should water leaks occur in the stator bars 15. When the probe 1 with an electrically insulative (e.g., non-metallic) handle 9 is placed on the surface 40 of the insulation 25, a capacitor is formed with the copper center 11 of the stator bar 15 as one capacitor plate and the active sensing surface 17 of the probe 1 as the other capacitor plate. The insulative handle 9 prevents introduction into the apparatus 100 of any interfering electric fields which could be coupled into the probe 1 by an operator. Said capacitor plates are generally referred to herein as electrically conductive plate elements.

Figure 4:
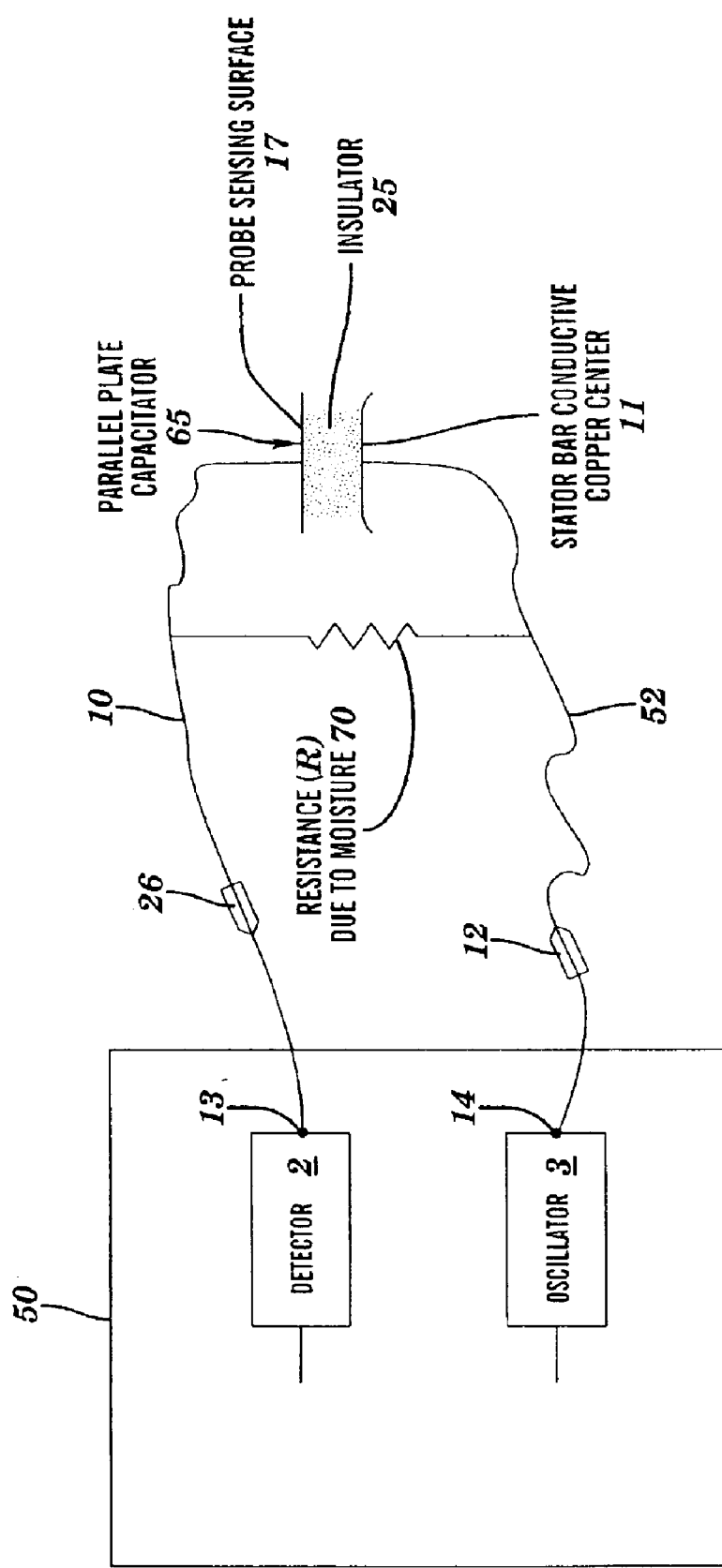
FIG. 4 depicts a parallel plate capacitor derived from FIG. 3, in accordance with embodiments of the present invention.

FIG. 4 depicts a parallel plate capacitor 65 derived from FIG. 3, in accordance with embodiments of the present invention. A parallel plate capacitor is defined herein, including in the claims, as comprising two electrically conductive surfaces, facing each other and essentially parallel to each other, such that electrically insulative material is disposed between said two electrically conductive surfaces. In FIG. 4, the parallel plate capacitor 65 comprises the insulation 25 serving as the capacitor dielectric interposed between the capacitor plates of the copper center 11 and the active sensing surface 17. The moisture in the insulation 25 also adds an electrically conductive path in parallel with the parallel plate capacitor 65, and said electrically conductive path is represented by the electrical resistance 70, denoted as R which is equivalent to an electrical conductance σ such that σ=1/R.

Figure 5:
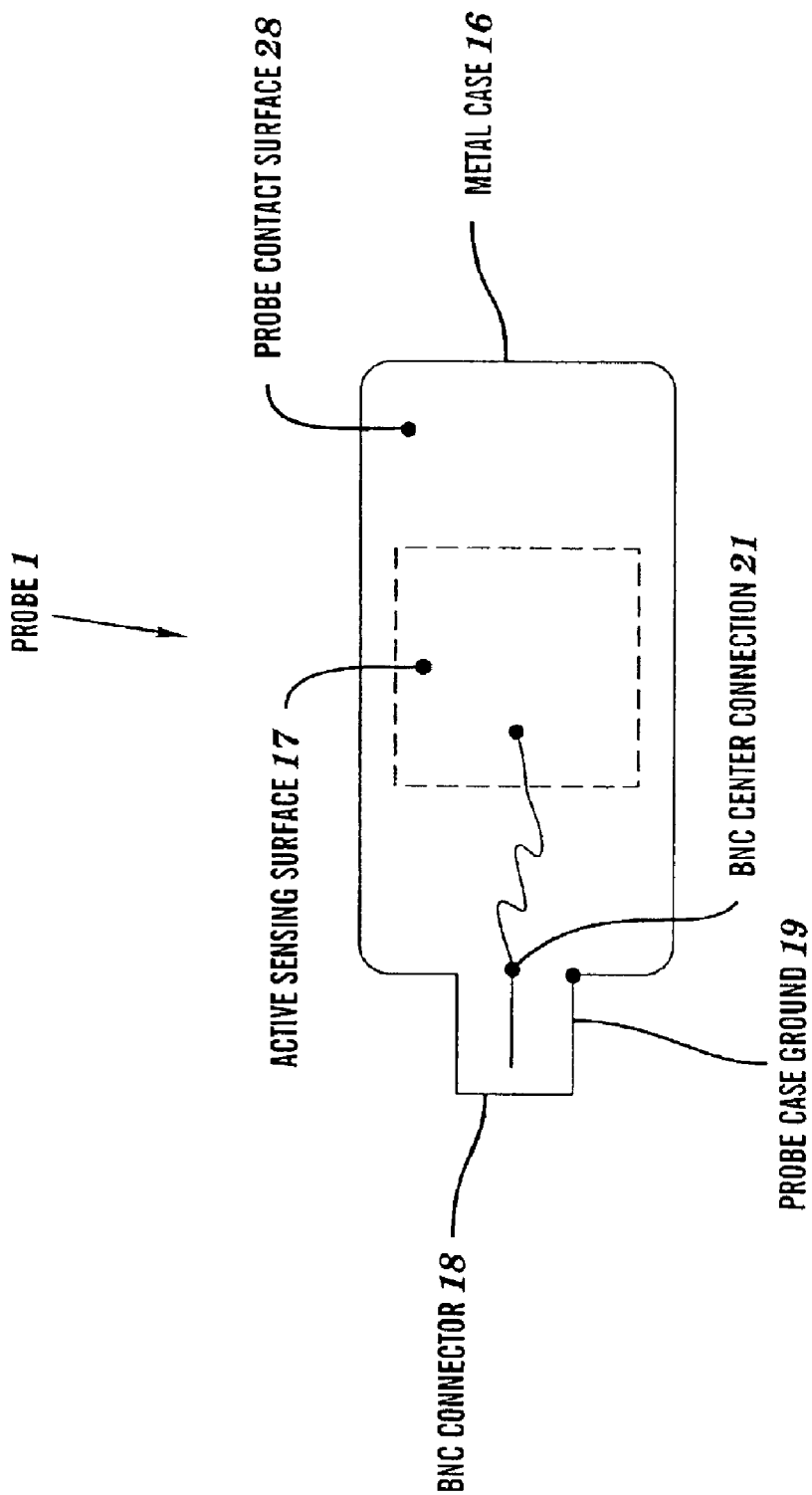
FIG. 5 depicts the probe of FIG. 1 enclosed in a small metallic case, in accordance with embodiments of the present invention.

FIG. 5 depicts the probe 1 enclosed in a small metallic case 16, in accordance with embodiments of the present invention. The metallic case 16 may have dimensions of, inter alia, 1 inch×2 inches×1 inch. An advantage of such a small probe: is that the probe 1 may be small enough to fit into a small space that would not otherwise be accessible to measurement with a larger probe; i.e., a space between an inner and outer layer where the probe 1 could sneak between items that need to have insulation resistance measured (e.g., a space in-between stator bars). Use of such a small probe may be the only way of measuring moisture for certain types of geometries.

In FIG. 5, the probe 1 has a non-metallic surface as a probe contact surface 28. A BNC Connector (i.e., British Naval Connector/Bayonet Nut Connector/Bayonet Neill Concelman) 18 is mounted onto the metallic case 16 for signal connection and its outer shield ties to probe case ground 19. The active sensing surface 17 is in a central portion of the probe contact surface 28, and the active sensing surface 17 electrically connects to the BNC center connection 21.

Figure 6:
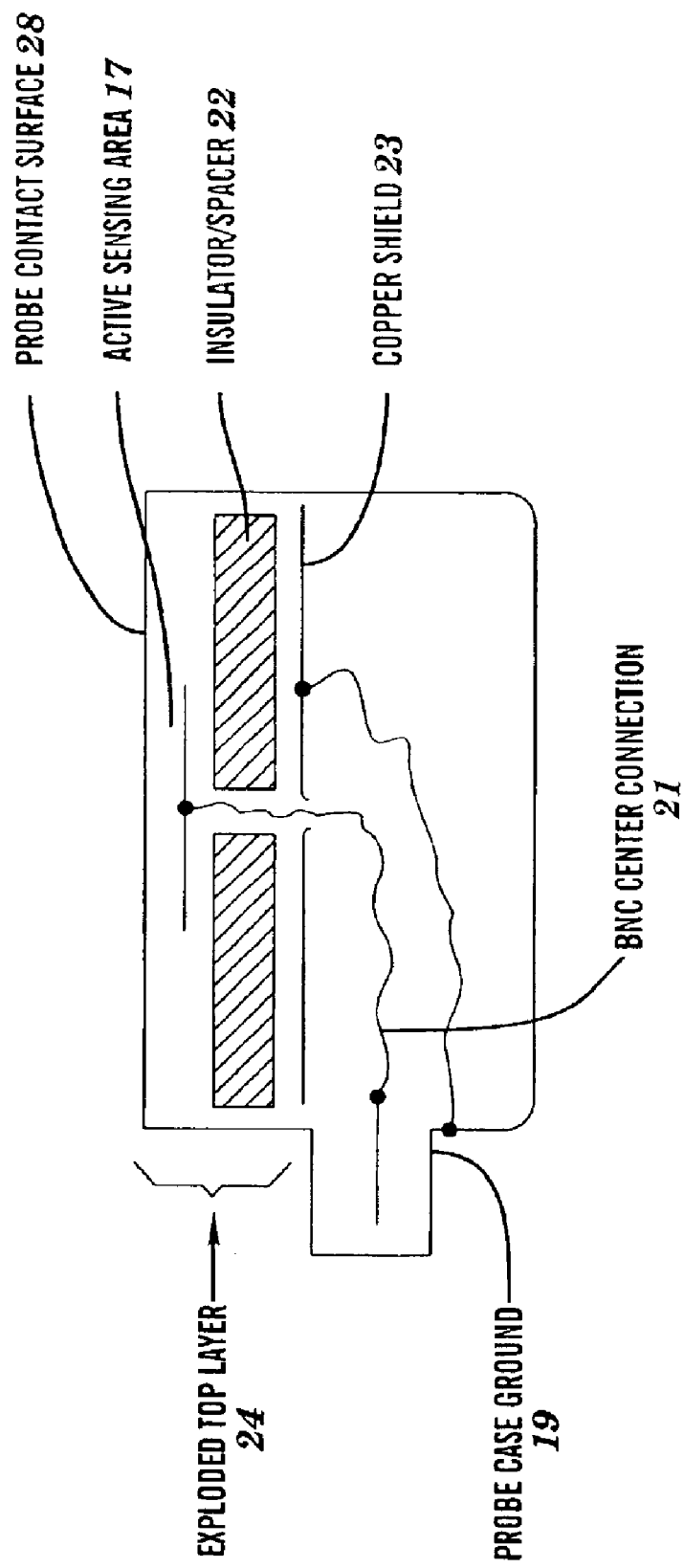
FIG. 6 depicts various layers within an exploded top layer of the probe of FIG. 5, in accordance with embodiments of the present invention.

FIG. 6 depicts various layers within an exploded top layer 24 of the probe 1 of FIG. 1, in accordance with embodiments of the present invention. In FIG. 6, the non-metallic probe contact surface 28 may have a thickness of, inter alia, about 0.010 inches. Beneath this is the active sensing surface/area 17, which could measure, inter alia, about 1 inch ×1 inch and may be formed from a thin deposit of copper onto an insulator/spacer 22 lying directly beneath. On the bottom side of the insulator/spacer 22 is deposited a thin layer of copper to form a copper shield 23. An electrical connection ties the copper shield 23 to the probe case ground 19.

"Conductance" Embodiments (FIGS. 7–16)

Figure 7:
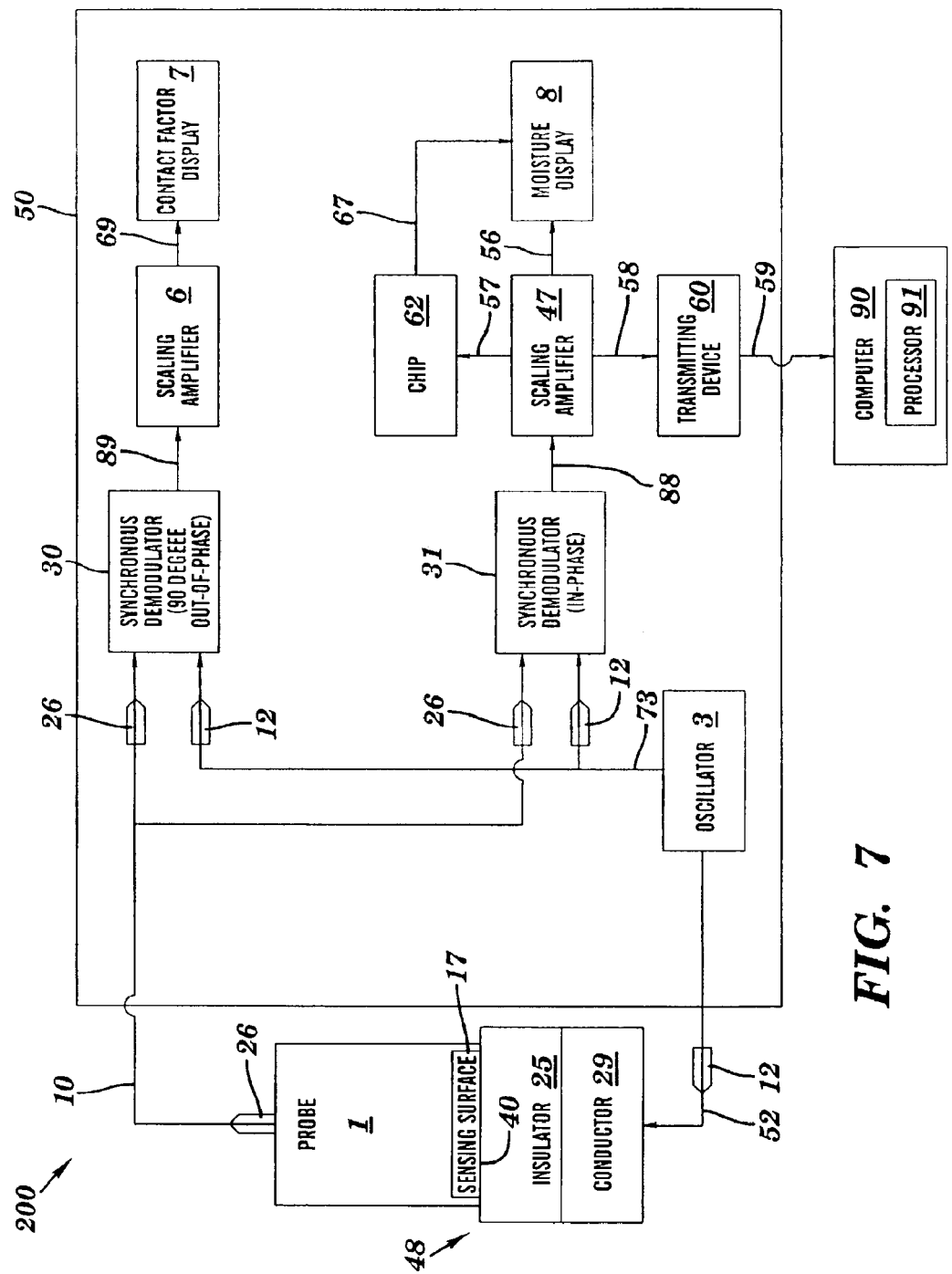
FIG. 7 is a block diagram of an apparatus having two synchronous demodulators for detecting moisture using an external probe, in accordance with embodiments of the present invention.

FIG. 7 is a block diagram of an apparatus 200, in accordance with embodiments of the present invention. The apparatus 200 includes an oscillator 3, synchronous demodulators 30 and 31, a scaling amplifier 6, a scaling amplifier 47, a moisture display 8, a semiconductor chip 62, and a transmitting device 60, all of which is enclosed within enclosure 50. The apparatus 200 further includes a probe 1 which is electrically coupled to the synchronous demodulators 30 and 31 via electrical connection 10 (e.g., cable). Additionally, the apparatus 200 may be powered by any voltage source (e.g., a battery pack). FIG. 7 also shows a body 48, which is generally a mass of matter, said body 48 comprising insulation 25 and an electrical conductor 29. An example of the body 48 is the power generator 27, discussed supra in conjunction with FIG. 2. The insulation 25 comprises an electrically insulative material. The apparatus 200 is adapted to detect and display, inter alia, moisture in the insulation 25 of the body 48.

In FIG. 7, the oscillator 3 is electrically coupled to the synchronous demodulators 30 and 31 via electrical connection 73. The oscillator 3 generates a reference signal 12 and transmits the signal 12 to the synchronous demodulators 30 and 31. The signal 12 is an oscillatory signal (e.g., a sinusoidal signal) which is also denoted symbolically as $S_1$. The signal 12 (i.e., $S_1$) is also propagated along the electrical connection 52 (e.g., cable) from the oscillator 3 into the body 48; i.e., into the electrical conductor 29 and then through the insulation 25 to the exterior surface 40 of the insulation 25, said surface 40 also being the exterior surface of the body 48. The signal 12 may comprise a frequency from 1 Khz to 50 Mhz. The probe 1 has an active sensing area/surface 17 for receiving the signal 12 from the surface 40 of the insulation 25. The signal 12 is denoted as the signal 26, or symbolically as $S_2$, as said signal emerges from the surface 40 and is received by the probe 1. After the signal 26 (i.e., $S_2$) is received by the probe 1, the signal 26 is detected and processed by the synchronous demodulators 30 and 31. Thus the synchronous demodulator 30 processes the signals 12 and 26 (i.e., $S_1$ and $S_2$). Likewise, the synchronous demodulator 31 processes the signals 12 and 26 (i.e., $S_1$ and $S_2$).

As discussed supra in conjunction with FIG. 4, moisture in the insulation 25: 1) adds additional capacitance in the parallel plate capacitor 65; and 2) adds an electrically conductive path in parallel with the capacitor 65 represented by the electrical resistance 70, denoted as R or equivalent electrical conductance $\sigma$, wherein $\sigma$ is a function (e.g., an increasing function) of the moisture content along a path traversed by $S_1$ within the insulation 25. As a consequence of moisture in the insulator 25, the test signal 26 (i.e., $S_2$) has: 1) an in-phase component $V_{IN}$ (due to $\sigma$ or the finiteness of R) relative to the reference signal 12 or $S_1$; and 2) a 90-degree out-of-phase component $V_{90}$ relative to the reference signal 12 or $S_1$. Definitionally, the 90-degree out-of-phase component $V_{90}$ of the test signal $S_2$ is understood to mean, herein and in the claims, the 90-degree out-of-phase component relative to $S_1$. If no moisture is present in the insulation 25 (which characterizes the purely dry state), then $\sigma=0$ (or equivalently, R is essentially infinite) and the insulation 25 has an impedance that includes pure capacitive reactance and infinite electrical resistance.

The synchronous demodulator 31 receives signals $S_1$ and $S_2$ as input, and determines the in-phase component $V_{IN}$ of $S_2$ relative to $S_1$. The determined in-phase component $V_{IN}$ of $S_2$ is a function of $\sigma$ (e.g., proportional to $\sigma$) and is thus may be an increasing function of the moisture content along a path traversed by $S_1$ within the insulation 25. The in-phase component $V_{IN}$ is transmitted via the electrical connection 88 to the scaling amplifier 47 that converts or amplifies $V_{IN}$ to yield a measure M of the moisture (e.g., moisture density distribution, moisture weight, moisture volume, etc.) along a path traversed by $S_1$ within the insulative material of the insulation 25. Amplification of $V_{IN}$ by the scaling amplifier 47 serves to provide an adequate signal level for subsequent display by the moisture display 8. The measure M is passed along electrical path 56 to the moisture display 8 where M is displayed. The measure M received by the moisture display 8 from the scaling amplifier 47 is $V_{IN}$ or a quantity that is proportional to $V_{IN}$. However, if $V_{IN}$ or a multiple thereof is passed to the semiconductor chip 62, such that the chip 62 is a compute element capable of performing computations, or more generally capable of executing an algorithm hard-coded therewithin, then the chip 62 may compute M to be generally be any desired function of $V_{IN}$ (e.g., the average water density within the insulation 25, the wight or volume within the insulation 25, the finite electrical resistance introduced by the moisture within the insulation 25, etc). Generally, M is a function (e.g., an increasing function) of $V_{IN}$. The chip 62 passes M along electrical path 67 to the moisture display 8 where M is displayed.

Alternatively, the measure M (e.g., $V_{IN}$ or a multiple thereof) may be transmitted along electrical path 58 into a transmitting device 60, which transmits M over a communication path 59 to a remote computer system 90. The computer system 90 is considered to be a remote computer system if the computer system 90 is external to the enclosure 50. The communication path 59 may be a wired path or a wireless path, and may be any path that is known to a person of ordinary skill in the art (e.g., cable, telephone lines, an Internet path, an Intranet path, etc.). The computer system 90 includes a processor 91 which may execute an algorithm that computes any desired function of the measure M. Said function of the measure M may include: the average water density within the insulation 25, the weight or volume within the insulation 25, the electrical conductance (or finite electrical resistance) introduced by the moisture within the insulation 25, etc). Additionally, The computer system 90 may store any such measured data received from the transmitting device 60, for later use such as, inter alia, graphically displaying at the computer system 90 how $V_{IN}$ or a function thereof varies over a series of transmissions of such measured data, transmitted to the computer system 90 over a period of time. FIG. 17 depicts the computer system 90 in detail as has been described supra.

The synchronous demodulator 30 receives signals $S_1$ and $S_2$ as input, and determines the 90-degree out-of-phase component $V_{90}$ of $S_2$ relative to $S_1$. The determined 90-degree out-of-phase component $V_{90}$ of $S_2$ is proportional to the capacitance and is denoted herein as a contact factor CF representing the degree of physical contact between the active sensing surface 17 of the probe 1 and the insulation 25 of the body 48. The 90-degree out-of-phase component $V_{90}$ is also called the "capacitive component" of $S_2$. Amplification of $S_2$ by the scaling amplifier 6 serves to provide an adequate signal level for subsequent display by the contact factor display 7. The contact factor CF is passed along electrical path 69 from the scaling amplifier 6 to the contact factor display 7 where CF is displayed. The contact factor CF received by the contact factor display 7 from the scaling amplifier 6 is the magnitude of the signal $S_2$ or a multiple thereof. Note that CF may be passed to a semiconductor chip or transmitting device (not shown in FIG. 7) in a manner that is analogous to the transmission of M to the chip 62 or the transmitting device 60, such that any function of CF may be computed and displayed.

An advantage of this synchronous modulation method described supra in conjunction with FIG. 7 is that the in-phase component $V_{IN}$ (which relates to moisture level in the insulation 25) is measured essentially independently from the out-out-phase component $V_{90}$ (which relates to the contact factor CF). Thus, the synchronous modulation method has the advantage of not being very sensitive to surface contact between the probe 1 and the insulation 25 for detection and measurement of moisture content. An additional feature of a synchronous detection method is that such synchronous modulation detection has an inherent noise immunity, because only signals of the desired frequency are detected, so that electrical noise (e.g., a 60 hz signal) is rejected.

Figure 8:
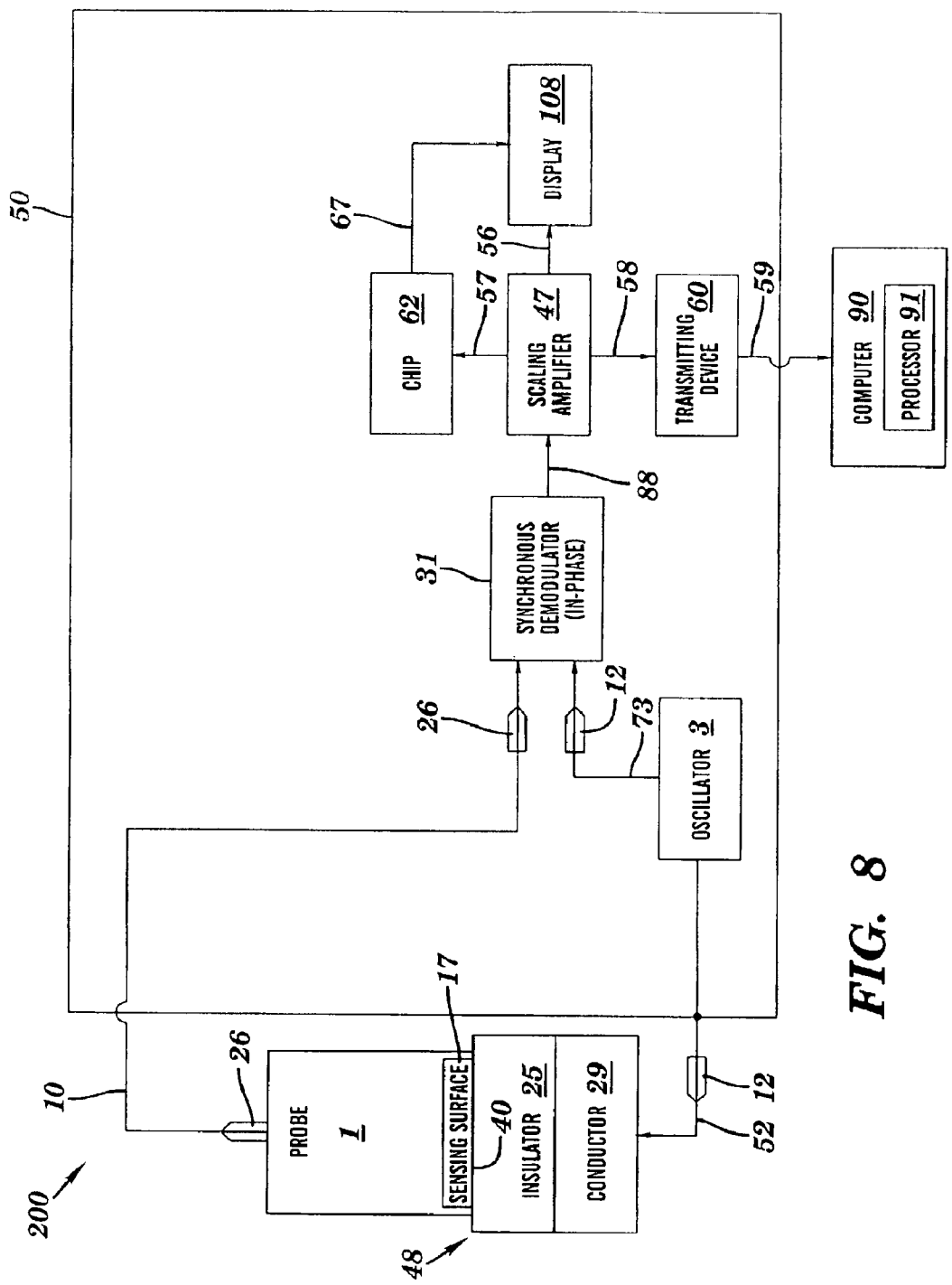
FIG. 8 depicts the apparatus of FIG. 7 with elimination of one of the synchronous demodulators, in accordance with embodiments of the present invention.

FIG. 8 is a block diagram of an apparatus 210, in accordance with embodiments of the present invention. The apparatus 210 of FIG. 8 is the similar to the apparatus 200 of FIG. 7, with elimination of the synchronous demodulator 30, the scaling amplifier 6, and the contact factor display 7 of FIG. 7. Additionally, the synchronous demodulator 31 in FIG. 8 includes an internal switch that has two settings, namely a first setting and a second setting. In the first setting of the internal switch, the synchronous demodulator 31 calculates $V_{IN}$. In the second setting of the internal switch, the synchronous demodulator 30 calculates $V_{90}$ which enables the contact factor CF to be determined. The internal switch may be any switch known to a person of ordinary skill in the art to accomplish the aforementioned functionality. The display 108 replaces the moisture display 8 of FIG. 7. In FIG. 8, the display 108 displays the measure M of moisture in response to a calculation of $V_{IN}$ by the synchronous demodulator 31, or alternatively the display 108 displays the contact factor CF in response to a calculation of $V_{90}$ by the synchronous demodulator 31.

Figure 9:
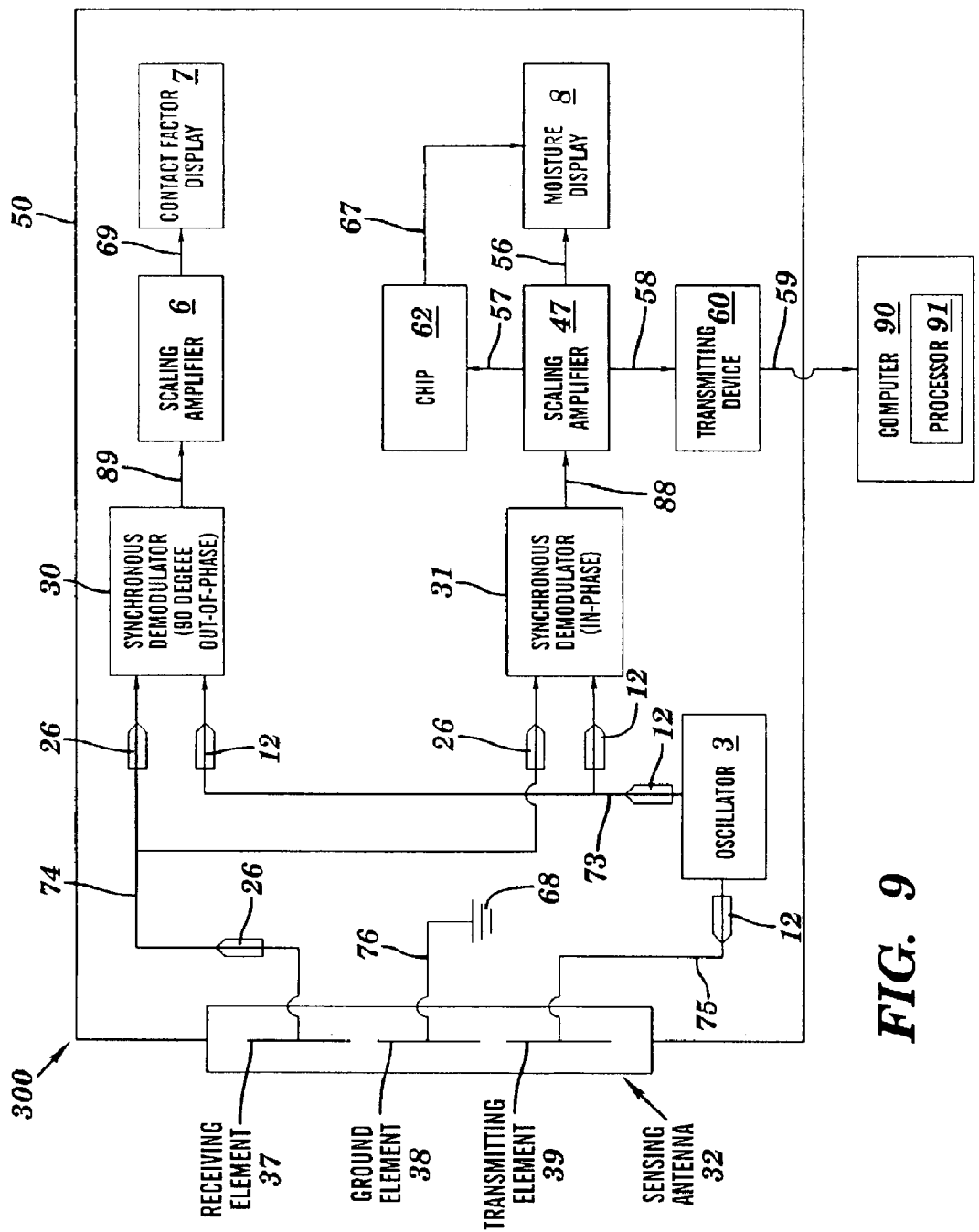
FIG. 9 is a block diagram of an apparatus having two synchronous demodulators for detecting moisture using a sensing antenna, in accordance with embodiments of the present invention.

FIG. 9 is a block diagram of an apparatus 300, in accordance with embodiments of the present invention. The apparatus 300 of FIG. 9 is similar to the apparatus 200 of FIG. 7, with the exception that the apparatus 300 of FIG. 9 uses a sensing antenna 32 instead of the probe 1 as the "sensing part". Unlike the probe 1 of FIG. 7 which is electrically coupled to the oscillator 3 and synchronous demodulators 30 and 31 via electrical connections 10 and 52 (e.g., cables) external to the enclosure 50, the sensing antenna 32 is coupled to the oscillator 3 and synchronous demodulators 30 and 31 without the use of electrical connections external to the enclosure 50. In particular, the sensing antenna 32 comprises a transmitting element 39, a receiving element 37 comprising a sensing surface, and a ground element 38. The transmitting element 39 is electrically coupled to the oscillator 3 through an internal electrical connection 75 that is essentially totally within the enclosure 50. The ground element 38 is electrically connected to a ground potential 68. The receiving element 37 is electrically coupled to the synchronous demodulators 30 and 31 through an internal electrical connection 74 that is essentially totally within the enclosure 50.

The oscillator 3 generates the reference signal 12 (i.e., $S_1$) and transmits the signal 12 to the body 48 (see supra FIG. 7 and infra FIG. 11 for the body 48) via the electrical connection 75 to the transmitting element 39. After the signal 12 propagated from the transmitting element 39 passes through the body 48 in the same manner as was described supra in conjunction with FIG. 7, the signal 12 emerges from the body 48 as the signal 26 (i.e., $S_2$) and is received by the receiving element 37. The signal 26 is propagated from the receiving element 37 to the synchronous demodulators 30 and 31 via the electrical connection 74. The sensing antenna 32 may be viewed as a "sensing part", since the sensing antenna 32 includes the receiving element 37 for receiving the signal 26 emerging from the body 48. The surface areas of apparatus 300, the transmitting element 39, the receiving element 37, and the ground element 38 are sufficiently small so as to be essentially capacitatively uncoupled to any electrical potential external to the enclosure 50. All electrically conductive surfaces within the enclosure 50 are essentially capacitatively uncoupled to any electrical potential external to the enclosure 50.

Aside from the replacement of the probe 1 by the sensing antenna 32, and the absence of cables external to the enclosure 50, the apparatus 300 of FIG. 9 is essentially the same as the apparatus 200 of FIG. 7 in the other respects. Elimination of cables external to the enclosure 50 may advantageously prevent undesirable electrical coupling to the apparatus 300. These cables may function like antennas floating near the body of an operator or the metal frame of any nearby object. Getting rid of the cables eliminates capacitive and inductive coupling due to signals radiating from the wires of the cables. In addition, without the cables there is a smaller likelihood of picking up electromagnetic interference that could affect the measurements of the apparatus 300. To eliminate body coupling, the measurement displays 7 and 8 reside in the same enclosure 50. Additionally, an electrically insulative (e.g., non-metallic) handle 45 (see infra FIG. 13) may be used to position the unit on a surface to be tested for moisture. The electrically insulative material of the handle 45 prevents the handle 45 from adding capacitative coupling to the apparatus 300. Note that the apparatus 300 may be small enough to be hand-held. A non-limiting example of the dimensions of the enclosure 44 is 3¾ in.×2 in.×⅞ in. The small size of the apparatus 300, especially the very small conductive surface areas of the apparatus 300, together with the insulative aspect of the handle 45, causes the apparatus 300 to be essentially capacitatively uncoupled to any electrical potential external to the enclosure 50, thus asllowing a more accurate measurement of moisture and contact factor.

Figure 10:
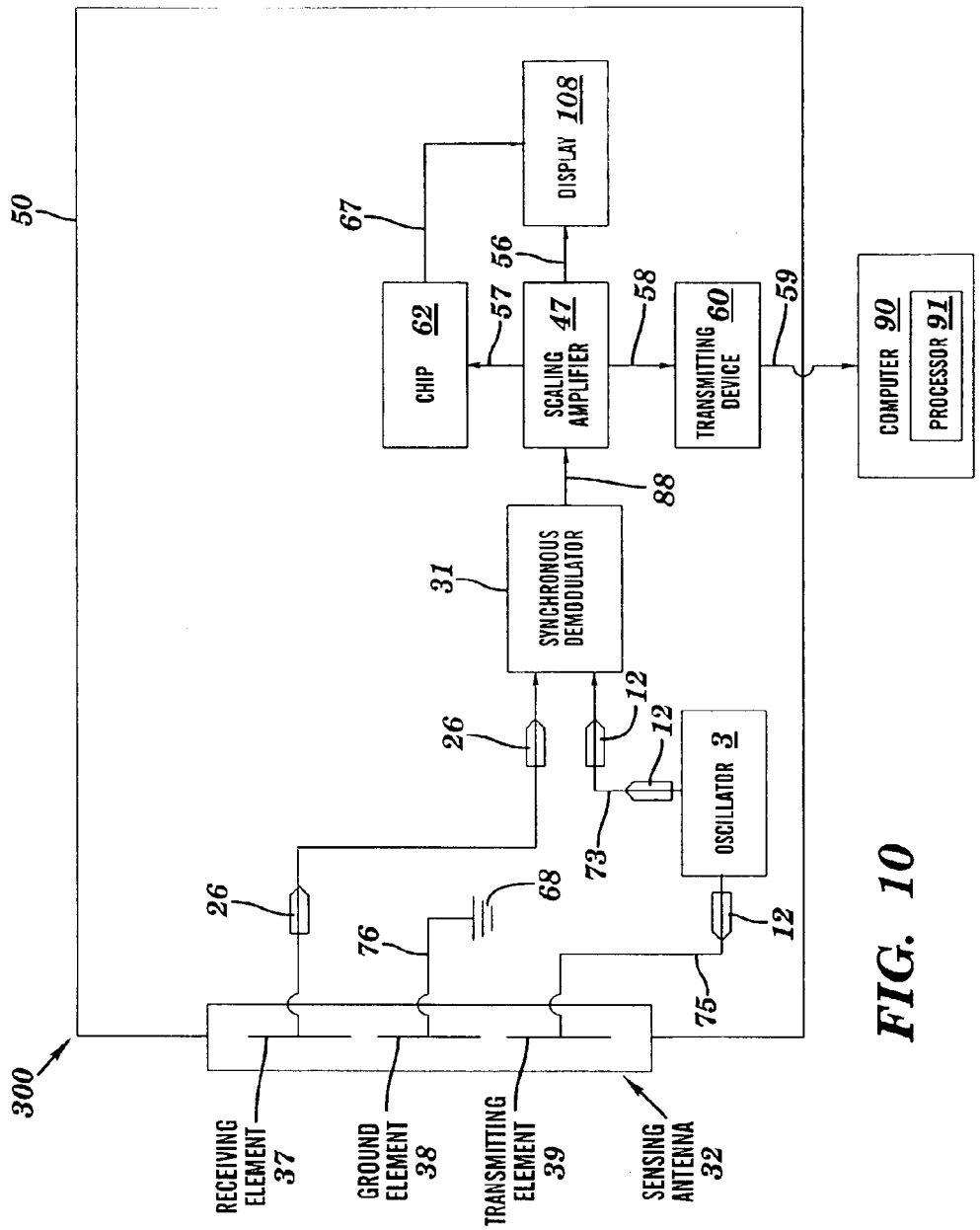
FIG. 10 depicts the apparatus of FIG. 9 with elimination of one of the synchronous demodulators, in accordance with embodiments of the present invention.

FIG. 10 is a block diagram of an apparatus 310, in accordance with embodiments of the present invention. The apparatus 310 of FIG. 10 is the similar to the apparatus 300 of FIG. 9, with elimination of the synchronous demodulator 30, the scaling amplifier 6, and the contact factor display 7 of FIG. 9. Additionally, the synchronous demodulator 31 in FIG. 10 includes an internal switch that has two settings, namely a first setting and a second setting. In the first setting of the internal switch, the synchronous demodulator 31 calculates $V_{IN}$. In the second setting of the internal switch, the synchronous demodulator 30 calculates $V_{90}$ which enables the contact factor CF to be determined. The internal switch may be any switch known to a person of ordinary skill in the art to accomplish the aforementioned functionality. The display 108 replaces the moisture display 8 of FIG. 9. In FIG. 10, the display 108 displays the measure M of moisture in response to a calculation of $V_{IN}$ by the synchronous demodulator 31, or alternatively the display 108 displays the contact factor CF in response to a calculation of $V_{90}$ by the synchronous demodulator 31.

Figure 11:
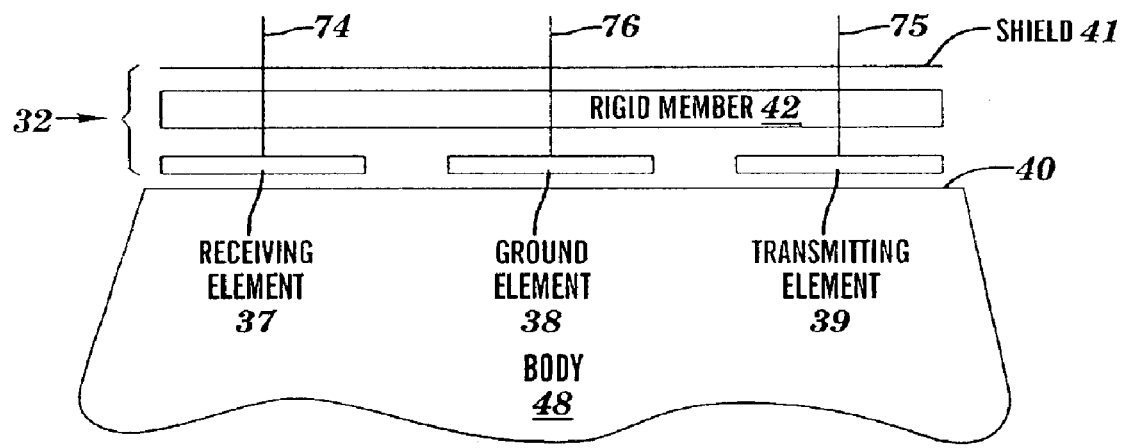
FIG. 11 depicts in greater detail the sensing antenna of the apparatus of FIGS. 9 and 10, in accordance with embodiments of the present invention.

FIG. 11 depicts the sensing antenna 32 of FIGS. 9 and 10 in greater detail. The assembly of the sensing antenna 32 comprises the elements (i.e., transmitting element 39, the receiving element 37, the ground element 38), and a shield 41 mounted on mounted on a rigid member 42 as shown. The insulated shield 41 connects to ground (not shown). The sensing antenna 32 assembly is shown on the surface 40 of the body 48. The ground element 38 separates the transmitting element 39 from the receiving element 37 as illustrated in the probe transmission system of FIG. 16.

Figure 16:
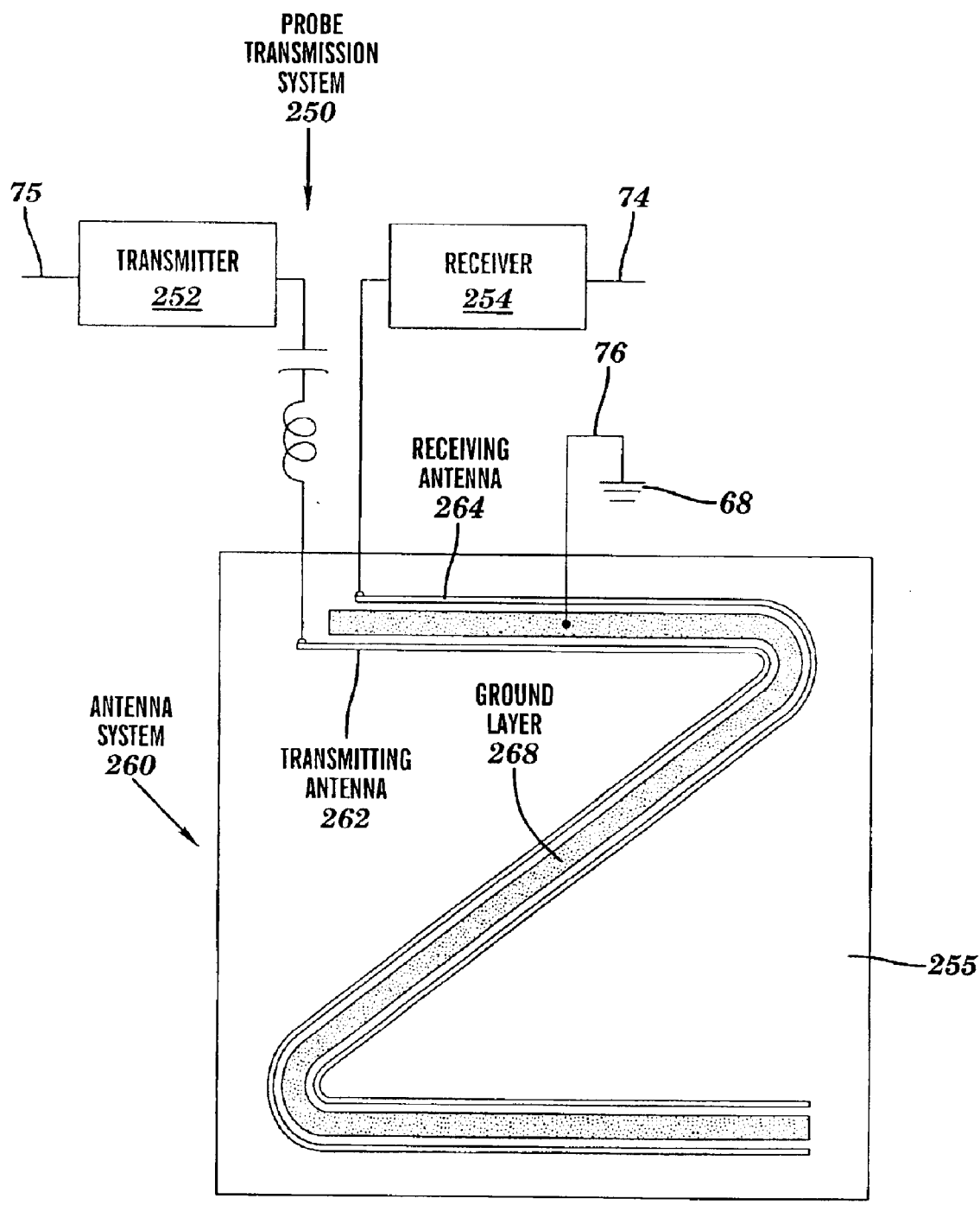
FIG. 16 depicts a probe transmission system, in accordance with embodiments of the present invention.

FIG. 16 depicts a probe transmission system 250, in accordance with embodiments of the present invention, and as described in U.S. Pat. No. 6,400,161 (Geisel, Jun. 04, 2002), incorporated herein by reference in its entirety. The probe transmission system 250 has a probe surface 255 on which is disposed a two-conductor transmission line of an antenna system 260 (analogous to the sensing antenna 32 of FIGS. 9–11) that includes a grounded conductor layer 268 interposed between a transmitting antenna 262 and the receiving antenna 264. The transmitting element 39 of FIG. 11 comprises the transmitting antenna 262 inductively and capacitively coupled to a transmitter 252 of FIG. 16. The receiving element 37 of FIG. 11 comprises the receiving antenna 264 electrically coupled to a receiver 254 of FIG. 16. The ground element 38 of FIG. 11 comprises the ground layer 268 electrically coupled to the ground 68 of FIG. 16.

Figure 12:
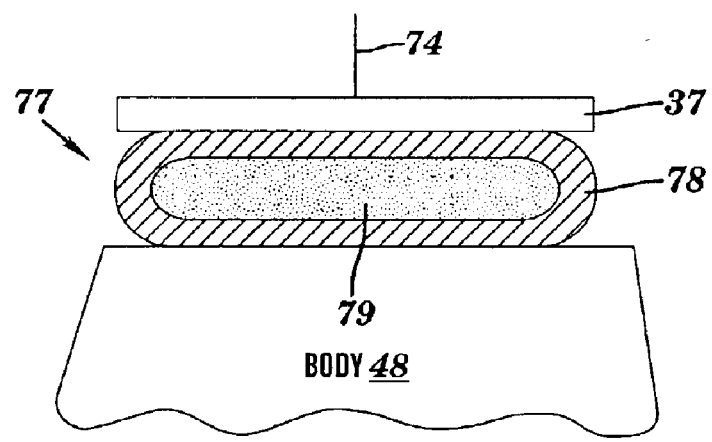
FIG. 12 depicts the receiving element of the sensing antenna of FIG. 11 electrically coupled to a body by a conductive interface disposed between the receiving element and the body, in accordance with embodiments of the present invention.

FIG. 12 depicts the receiving element 37 of FIG. 11 electrically coupled to the body 48 by a conductive interface 77 disposed between the receiving element 37 and the body 48, in accordance with embodiments of the present invention. The conductive interface 77 may be any flexible conductive interface that includes a electrically conductive wrapping 78 (e.g., a fine silver braid) around a flexible foam material 79. An example of the conductive interface 77 is a gasket which includes a foam center wrapped with very fine silver braid. While FIG. 12 shows the flexible conductive interface 77 disposed between the receiving element 37 and the body 48, such a flexible conductive interface may be similarly disposed between the transmitting element 39 of FIG. 11 and the body 48. Alternatively, the conductive interface 77 may exclude the foam material 79. For example, the conductive interface 77 may be spatially uniform and consist of one electrically conductive material such as a metal or a metallic alloy, or a flexible electrically conductive polymer.

Figure 13:
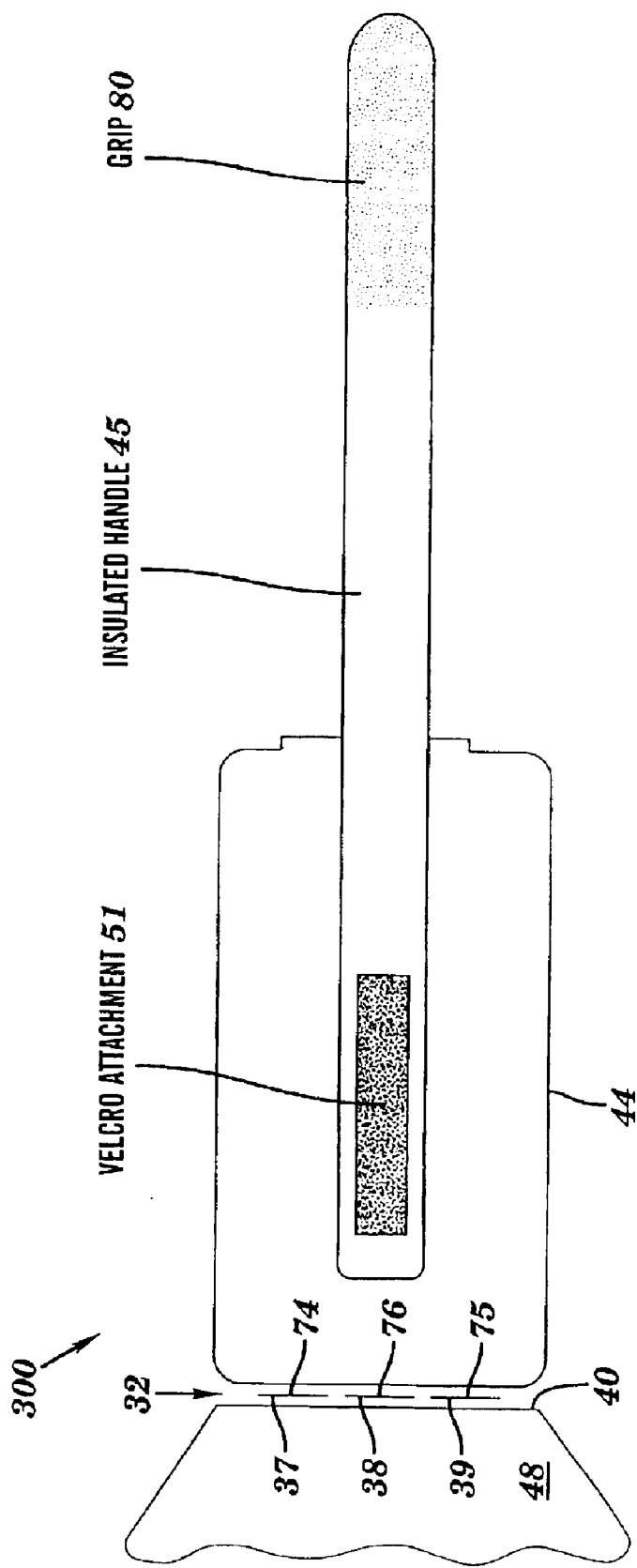
FIG. 13 depicts the apparatus of FIGS. 9 and 10 with an added insulative handle attached to the apparatus, in accordance with embodiments of the present invention.

FIG. 13 depicts the apparatus 300 of FIGS. 9 and 10, in accordance with embodiments of the present invention. The sensing antenna 32 is sensing the surface 40 of the body 48 using the transmitting element 39, the receiving element 37, and the ground element 38. The apparatus 300 has a plastic enclosure 44 and an electrically insulative (e.g., non-metallic) handle 45. The handle 45, which has a grip 80 at its end, is mechanically attached to the enclosure 44 by a velcro attachment 51. The handle 45 can be manipulated by a user of the apparatus to move the sensing antenna 32 into contact with the body 48. The handle 45 is described in U.S. Pat. No. 6,400,161 (Geisel, Jun. 04, 2002), incorporated herein by reference in its entirety.

Figure 14:
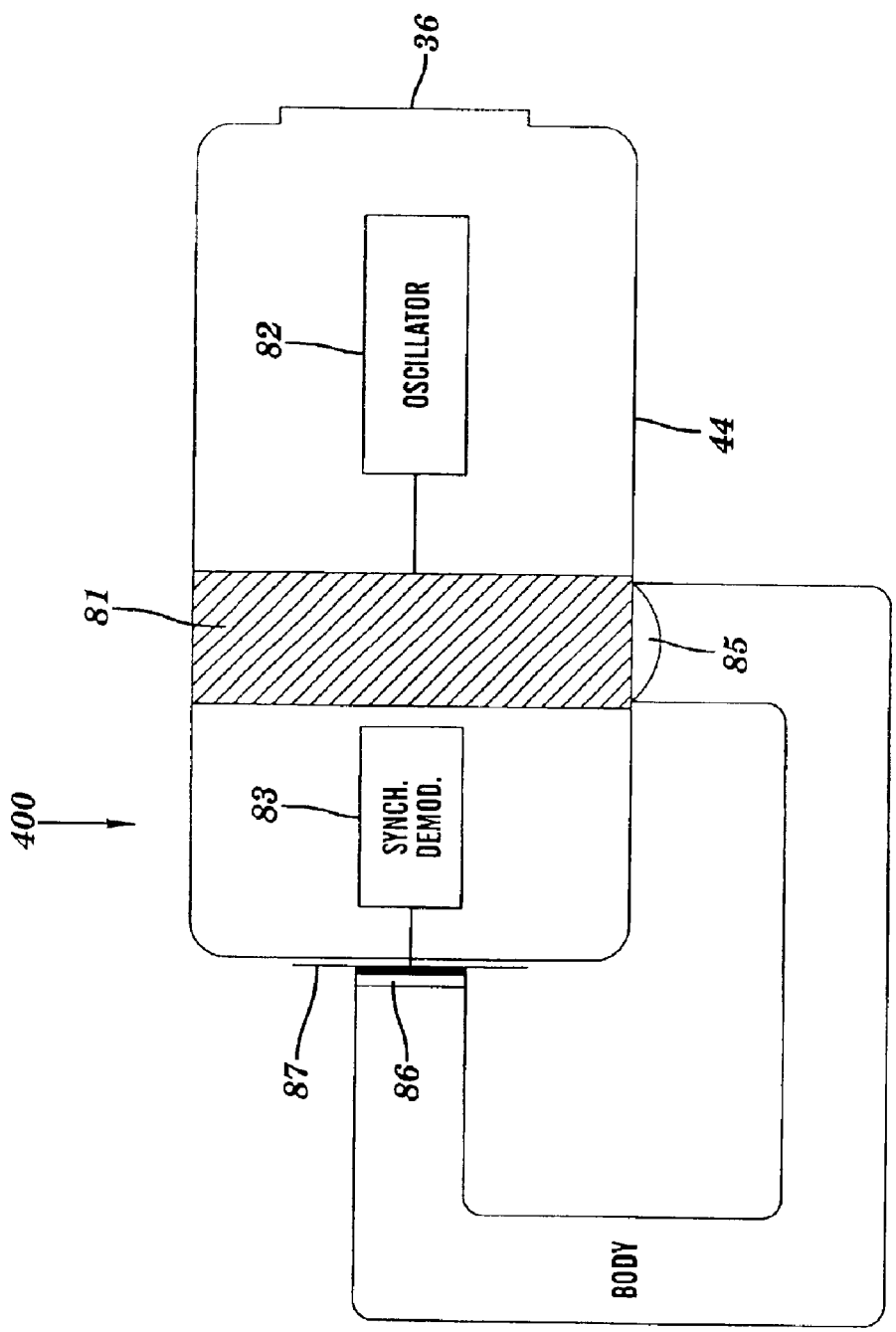
FIG. 14 depicts a variation in the apparatus of FIGS. 9 and 10 such that the transmitting element of the apparatus includes a conductive band around the apparatus, in accordance with embodiments of the present invention.

FIG. 14 depicts an apparatus 400 representing a variation in the apparatus of 300 of FIG. 9, in accordance with embodiments of the present invention. An essential difference between the apparatus 400 of FIG. 14 and the apparatus 300 of FIG. 9 is the difference in the respective probe configurations. In FIG. 14, the probe comprises a transmitting element 81 and a receiving element 87 as shown. The transmitting element 81 is a conductive band around the electrically nonconductive (e.g., plastic) enclosure 44 that encloses the apparatus 400. The receiving element 87 comprises a receiving antenna and may also include a flexible conductive interface similar to the flexible conductive interface 77 shown in FIG. 12 and described supra. The synchronous demodulator 83 is coupled to the receiving element 87 in a manner analogous to the coupling of the synchronous demodulator 83 is coupled to the synchronous demodulator 31 to the receiving element 37 in FIG. 9. The apparatus 400 may be used for detecting local moisture content at various skin surface locations 86 on the body 85 of a person, and displaying a measure M of the moisture content in the digital moisture display 36. The apparatus 400 is designed to be held by a hand 85 of the person, by grasping the conductive band 81. A non-limiting example of the dimensions of the enclosure 44 is 3¾ in.×2 in.×⅛ in. The oscillator 82 delivers a micro level transmitting signal to the conductive band 81 while the hand 85 is grasping the conductive band 81. The oscillator signal travels via hand 85 and arm, throughout the person's entire body and the entire body skin surface. A single sensing element, namely the receiving element 87, picks up this signal when the receiving element 87 is placed in contact with the skin surface locations 86. Thus, the apparatus 400 is well-suited to detect and measure local skin moisture. This approach is very similar to the oscillator signal being connected to a generator frame as is shown in FIG. 2 and described supra. The person's body 86 is energized with the oscillator signal similar to energizing the generator frame. The apparatus 400 measures the skin moisture perpendicularly, or through the skin.

In some embodiments, the apparatus 400 will have only the synchronous demodulator 83 for measuring moisture. In other embodiments, the apparatus 400 will also have another synchronous demodulator (analogous to the synchronous demodulator 30 in FIG. 9) for measuring and displaying the contact factor CF, either concurrently operating together with the synchronous demodulator 83 as in FIG. 9, or operating alternatively through a switch such as switch 72 shown in FIG. 10. Additionally, the apparatus 400 may have any of the other compatible features shown in FIG. 9 (e.g., chip 62, transmitting device 60, etc.).

Figure 15:
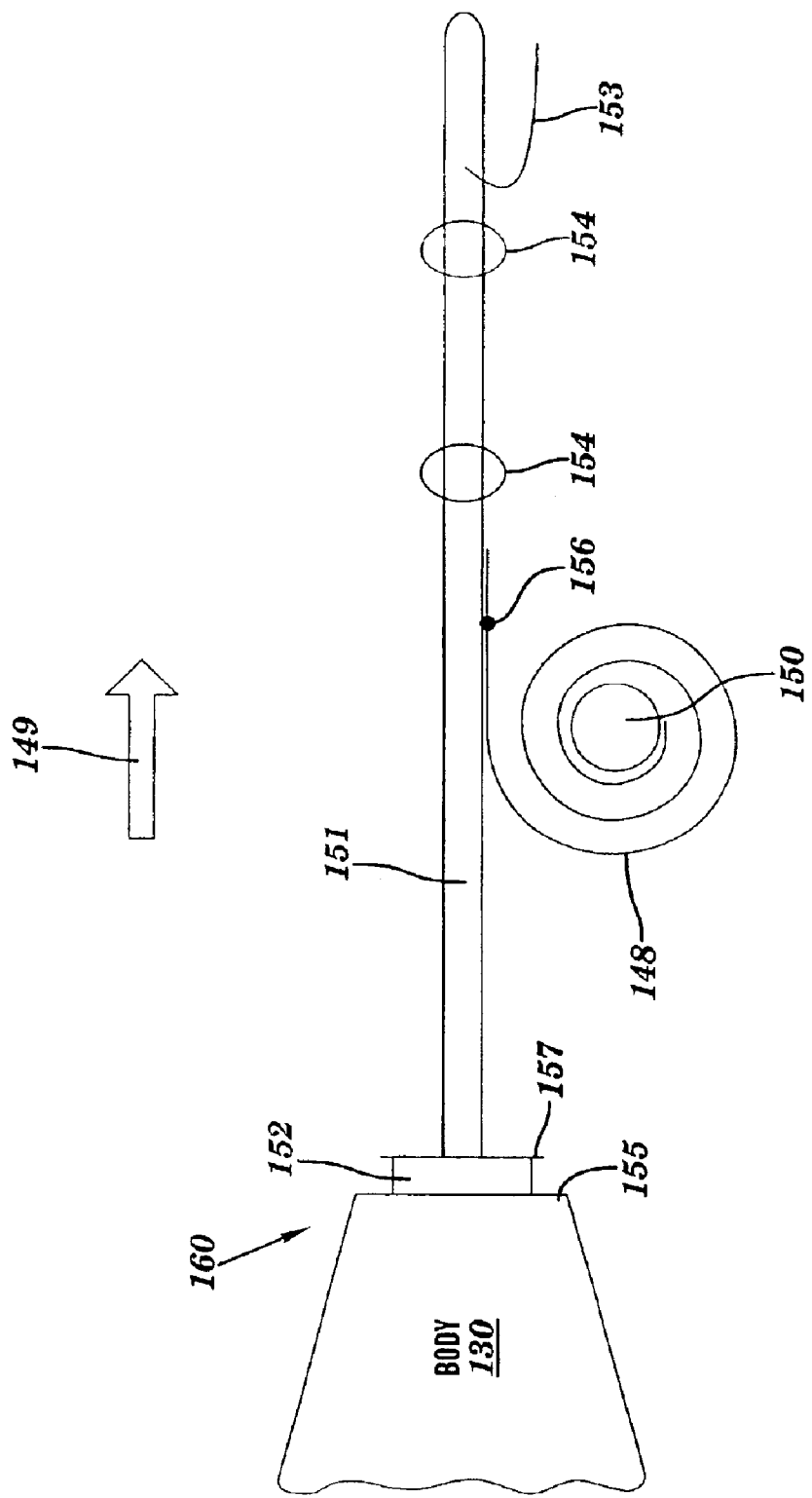
FIG. 15 depicts a constant-force assembly integrated with the apparatus of FIG. 14 for measuring moisture on skin surfaces, in accordance with embodiments of the present invention.

FIG. 15 depicts a constant-force assembly 160 integrated with the hand-held apparatus 400 of FIG. 14 for measuring moisture on surfaces such as skin surfaces of a body 130, in accordance with embodiments of the present invention. The constant-force assembly 160 includes a constant-force spring 148 provides for making repeatable measurements of a skin surface. The constant-force spring 148, which may include a non-metallic material, measures approximately ¼ inch in width and 0.01 inches in thickness, and is formed like a tape measure. The constant-force spring 148 travels to the right when extended, in direction 149 of travel. A mechanically fixed center guide 150 aligns and centers the spring 148, but is not attached to the constant-force spring 148. The constant-force spring 148 is affixed to a metallic rod 151 at a tie point 156. The metallic rod 151 travels within slide loops 154, which secure the metallic rod 151 while allowing travel in the direction 149. At the probing end of the metallic rod 151 is a flexible conductive interface 152 which is similar or essentially the same as the flexible conductive interface 77 depicted in FIG. 12 and described supra. The flexible conductive interface 152 is adapted to contact the surface 155 of the body 130. The interface 152 provides for a more repeatable contact with the surface 155 because it is compliant and fills in gaps even if the surface 155 flexes. The electrical connection 153 provides electrical coupling to a synchronous demodulator such as the synchronous demodulator 83 of the apparatus 400 in FIG. 14. The entire assembly 160 is contained in enclosure 44 (see FIG. 14) being affixed by center guide 150. When plastic enclosure 44 is pressed near the surface 155, the assembly 160 contacts the surface 155 and exhibits a fixed force on the surface 155 over a travel range of approximately ½ inch. Thus, the constant-force spring 148 provides a constant force on the surface 155, thereby maintaining the conductive contact surface area constant, which reduces variability in the measured electrical conductance due to moisture.

Those skilled in the art could use the teachings contained herein and substitute the disclosed phase/magnitude embodiments with disclosed conductance/capacitance embodiments to achieve numerous variations of the invention.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. An apparatus for detecting moisture, comprising:

an oscillator for generating a first oscillatory electrical signal $S_1$;

means for propagating $S_1$ into a body at an electrical conductor disposed entirely within the body and then along a linear path from the electrical conductor through an electrically insulative material disposed entirely within the body such that a signal due to $S_1$ emerges from the path and from the body as a second oscillatory electrical signal $S_2$;

a probe having an electrically conductive sensing surface adapted to be in physical contact with the body and to receive $S_2$, wherein the electrically insulative material is disposed between the sensing surface and the electrical conductor so as to form a parallel plate capacitor across which $S_1$ and $S_2$ differ in phase by $\Delta\phi$ such that $\Delta\phi$ is indicative of moisture along the entire path traversed by $S_1$ within the electrically insulative material; and a moisture detecting device adapted to determine $\Delta\phi$ from $S_1$ and $S_2$ and a measure M of the moisture based on M being proportional to $\Delta\phi$.

2. The apparatus of claim 1, wherein the moisture detecting device is further adapted to receive $S_1$ from the oscillator and $S_2$ from the probe, and to determine $\Delta\phi$ from $S_1$ and $S_2$.

3. The apparatus of claim 1, further comprising means for displaying M.

4. The apparatus of claim 1, further comprising means for determining from the magnitude of $S_2$ a measure of the degree of physical contact between the sensing surface and the body.

5. The apparatus of claim 4, further comprising means for displaying the measure of the degree of physical contact.

6. The apparatus of claim 1, wherein the probe is capable of being hand held.

7. The apparatus of claim 1, wherein the probe is within a metallic case, and wherein the metallic case does not electrically interfere with $S_2$.

8. The apparatus of claim 1, wherein $S_1$ has a frequency falling within a frequency range of 1 Khz to 50 Mhz.

9. The apparatus of claim 1, wherein the insulative material surrounds stator bars of a power generator, and wherein the stator bars comprise the electrical conductor.

10. The apparatus of claim 9, wherein the path traversed by $S_1$ includes a path segment from a copper center of the stator bars through the total thickness of insulative material to a location on an exterior surface of the body where $S_2$ emerges from the body.

11. The apparatus of claim 9, wherein the stator bars are ungrounded, and wherein $S_1$ is adapted to be coupled to any of the ungrounded stator bars by a sufficiently large capacitance between the stator bars and a generator frame ground of the power generator, without a DC ground path existing between a copper center of the stator bars and the generator frame ground.

12. A method for detecting moisture, comprising:
propagating a first oscillatory electrical signal $S_1$ into a body at an electrical conductor disposed entirely within the body and then along a linear path from the electrical conductor through an electrically insulative material disposed entirely within the body such that a signal due to $S_1$ emerges from the path and from the body as a second oscillatory electrical signal $S_2$;
receiving $S_2$ by an electrically conductive sensing surface of a probe, wherein the sensing surface is in contact with the body, and wherein the electrically insulative material is disposed between the sensing surface and the electrical conductor so as to form a parallel plate capacitor across which $S_1$ and $S_2$ differ in phase by $\Delta\phi$ such that $\Delta\phi$ is indicative of moisture along the entire path traversed by $S_1$ within the electrically insulative material; and
transmitting $S_2$ from the probe to a moisture detecting device that determines $\Delta\phi$ from $S_1$ and $S_2$ and a measure M of the moisture, based on M being proportional to $\Delta\phi$.

13. The method of claim 12, further comprising displaying M.

14. The method of claim 12, further comprising generating $S_1$ by an oscillator that is coupled to the moisture detecting device.

15. The method of claim 12, further determining from the magnitude of $S_2$ a measure of the degree of physical contact between the sensing surface and the body.

16. The method of claim 15, further comprising displaying the measure of the degree of physical contact.

17. The method of claim 12, wherein the probe is capable of being a hand held.

18. The method of claim 12, wherein the probe is within a metallic case, and wherein the metallic case does not electrically interfere with $S_2$.

19. The method of claim 12, wherein $S_1$ has a frequency falling within a frequency range of 1 Khz to 50 Mhz.

20. The method of claim 12, wherein the insulative material surrounds stator bars of a power generator, and wherein the stator bars comprise the electrical conductor.

21. The method of claim 20, wherein the path traversed by $S_1$ includes a path segment from a copper center of the stator bars through the total thickness of insulative material to a location on an exterior surface of the body where $S_2$ emerges from the body.

22. The method of claim 20, wherein the stator bars are ungrounded, and wherein $S_1$ is coupled to any of the ungrounded stator bars by a sufficiently large capacitance between the stator bars and a generator frame ground of the power generator, without a DC ground path existing between a copper center of the stator bars and the generator frame ground.

23. An apparatus for detecting moisture, comprising:
an oscillator for generating a first oscillatory electrical signal $S_1$;
means for propagating $S_1$ into a body such at an electrical conductor disposed entirely within the body and then along a linear path from the electrical conductor through an electrically insulative material disposed entirely within the body such that a signal due to $S_1$ emerges from the path and from the body as a second oscillatory electrical signal $S_2$;
a sensing part having an electrically conductive sensing surface adapted to be in physical contact with the body and to receive $S_2$, wherein the electrically insulative material is disposed between the sensing surface and the electrical conductor so as to form a parallel plate capacitor that is in electrical parallel with an electrically resistive path characterized by a conductance $\sigma$, and wherein $\sigma$ is indicative of moisture along the entire path traversed by $S_1$ within the electrically insulative material; and
a moisture detecting device adapted to determine from $S_1$ and $S_2$ a function of $\sigma$, wherein said function of $\sigma$ is a measure M of the moisture.

24. The apparatus of claim 23, wherein the moisture detecting device is further adapted to receive $S_1$ from the oscillator and $S_2$ from the sensing surface.

25. The apparatus of claim 23, further comprising means for displaying M.

26. The apparatus of claim 23, further comprising means for determining from the capacitive component of $S_2$ a measure of the degree of physical contact between the sensing surface and the body.

27. The apparatus of claim 26, further comprising means for displaying the measure of the degree of physical contact.

28. The apparatus of claim 23, further comprising transmitting means for transmitting to a compute element a signal comprising M.

29. The apparatus of claim 28, wherein the compute element is comprised by a computer system that is remote to an enclosure that encloses the oscillator and the moisture detecting device.

30. The apparatus of claim 28, wherein the compute element includes means for calculating from M the moisture, through deployment of an algorithm that utilizes a correlation between M and the moisture.

31. The apparatus of claim 23, wherein the insulative material surrounds stator bars of a power generator, and wherein the insulative material is disposed between the sensing surface and the stator bars so as to form a parallel plate capacitor.

32. The apparatus of claim 31, wherein the path traversed by $S_1$ includes a path segment from a copper center of the stator bars through the total thickness of insulative material to a location on an exterior surface of the body where $S_2$ emerges from the body.

33. The apparatus of claim 31, wherein the stator bars are ungrounded, and wherein $S_1$ is adapted to be coupled to any of the ungrounded stator bars by a sufficiently large capacitance between the stator bars and a generator frame ground of the power generator, without a DC ground path existing between a copper center of the stator bars and the generator frame ground.

34. An apparatus for detecting moisture, comprising:
    an oscillator for generating first oscillatory electrical signal $S_1$;
    means for propagating $S_1$ into a body such that a signal due to $S_1$ emerge from the body as a second oscillatory electrical signal $S_2$, wherein the body includes an electrically insulative material having a conductance $\sigma$, and wherein $\sigma$ is indicative of moisture along a path traversed by $S_1$ within the insulative material;
    a sensing part having an electrically conductive sensing surface adapted to be in physical contact with the body and to receive $S_2$; and
    a moisture detecting device adapted to determine from $S_1$ and $S_2$ a measure M of the moisture, said measure M being a function of $\sigma$, wherein the moisture detecting device comprises a first synchronous demodulator for determining the in-phase component $V_{IN}$ of $S_2$ relative to $S_1$, wherein M is a function of $V_{IN}$, and wherein $V_{IN}$ increases as $\sigma$ increases.

35. The apparatus of claim 34, wherein the apparatus further comprises an electrically insulative enclosure that encloses the oscillator and the moisture detecting device, and wherein the sensing part comprises a probe located external to the enclosure.

36. The apparatus of claim 34, wherein the apparatus further comprises an electrically insulative enclosure that encloses the oscillator and the moisture detecting device, wherein the sensing part comprises a sensing antenna, wherein the sensing antenna includes a transmitting element, a receiving element comprising the sensing surface, and a ground element, wherein the ground element is electrically connected to a ground potential within the enclosure, wherein the transmitting element is adapted to transmit $S_1$ to the body, wherein the receiving element is adapted to receive $S_2$ from the body, and wherein the apparatus is essentially capacitatively uncoupled to any electrical potential external to the enclosure.

37. The apparatus of claim 36, wherein the sensing antenna comprises a two-conductor transmission line that includes the grounded conductor interposed between the transmitting element and the receiving element.

38. The apparatus of claim 36, wherein the insulative material surrounds stator bars of a power generator.

39. The apparatus of claim 36, further comprising an electrically insulative handle mechanically connected to the enclosure, wherein the handle can be manipulated by a user of the apparatus to move the sensing surface into physical contact with the body.

40. The apparatus of claim 36, wherein the enclosure and its contents is capable of being hand held.

41. The apparatus of claim 36, further comprising a flexible conductive interface electrically connecting an element to the body, wherein the element is selected from the group consisting of the transmitting element, the receiving element, and the ground element.

42. The apparatus of claim 41, further comprising a constant-force assembly coupled to the flexible conductive interface so as to cause the flexible conductive interface to exert an approximately constant force on the body, wherein the constant-force assembly includes a constant-force spring.

43. The apparatus of claim 36, further comprising an electrically conductive band wrapped around the enclosure, wherein the conductive band includes the transmitting element.

44. The apparatus of claim 43, wherein a person comprises the body, wherein the enclosure and its contents is capable of being held at the band by a hand of a person, and wherein the sensing surface is adapted to be placed by said hand at a surface location on the skin of the person to determine M as a function of the surface location.

45. The apparatus of claim 34, further comprising a second synchronous demodulator for determining from $S_1$ and $S_2$ the 90-degree out-of-phase component $V_{90}$ of $S_2$ relative to $S_1$, wherein $V_{90}$ is a measure of the degree of physical contact between the sensing surface and the body.

46. The apparatus of claim 34, further comprising an internal switch within the first synchronous demodulator for switching $S_1$ and $S_2$ between a first switch setting and a second switch setting, wherein the first switch setting enables a determination of $V_{IN}$, wherein the second switch setting enables a determination the 90-degree out-of-phase component $V_{90}$ of $S_2$ relative to $S_1$, and wherein $V_{90}$ is a measure of the degree of physical contact between the sensing surface and the body.

47. A method for detecting moisture, comprising:
    propagating a first oscillatory electrical signal $S_1$ into a body at an electrical conductor disposed entirely within the body and then along a linear path from the electrical conductor through an electrically insulative material disposed entirely within the body such that a signal due to $S_1$ emerges from the path and from the body as a second oscillatory electrical signal $S_2$;
    receiving $S_2$ by a sensing surface of a sensing part, wherein the sensing surface is in physical contact with the body, and wherein the electrically insulative material is disposed between the sensing surface and the electrical conductor so as to form a parallel plate capacitor that is in electrical parallel with an electrical resistive path characterized by a conductance $\sigma$, and wherein $\sigma$ is indicative of moisture along the entire path traversed by $S_1$ within the electrically insulative material; and
    transmitting $S_2$ from the sensing surface to a moisture detecting device that determines from $S_1$ and $S_2$ a function of $\sigma$, wherein said function of a $\sigma$ is a measure M of the moisture.

48. The method of claim 47, further comprising:
    generating $S_1$ by an oscillator; and
    transmitting $S_1$ from the oscillator to the moisture detecting device.

49. The method of claim 47, further comprising displaying M.

50. The method of claim 47, further comprising determining from the capacitive component of $S_2$ a measure of the degree of physical contact between the sensing surface and the body.

51. The method of claim 50, further comprising displaying the measure of the degree of physical contact.

52. The method of claim 47, further comprising transmitting to a compute element a signal comprising M.

53. The method of claim 52, wherein said transmitting is performed by a transmitting device, and wherein the compute element is comprised by a computer system that is remote to an enclosure that encloses the moisture detecting device and the transmitting device.

54. The method of claim 52, wherein the method further comprises calculating from M the moisture using the compute element to perform said calculating, through deployment of an algorithm that utilizes a correlation between M and the moisture.

55. The method of claim 47, wherein the insulative material surrounds stator bars of a power generator, and wherein the insulative material is disposed between the sensing surface and the stator bars so as to form a parallel plate capacitor.

56. The method of claim 55, wherein the path traversed by $S_1$ includes a path segment from a copper center of the stator bars through the total thickness of insulative material to a location on an exterior surface of the body where $S_2$ emerges from the body.

57. The method of claim 55, wherein the stator bars are ungrounded, and wherein $S_1$ is adapted to be coupled to any of the ungrounded stator bars by a sufficiently large capacitance between the stator bars and a generator frame ground of the power generator, without a DC ground path existing between a copper center of the stator bars and the generator frame ground.

58. A method for detecting moisture, comprising;
propagating a first oscillator electrical signal $S_1$ into a body such that a signal due to $S_1$ emerges from the body as a second oscillatory electrical signal $S_2$ wherein the body includes an electrically insulative material having a conductance $\sigma$, and wherein $\sigma$ indicative of moisture along a path traversed by $S_1$ within the insulative material;
receiving $S_2$ by a sensing surface of a sensing part wherein the sensing surface is in physical contact with the body; and
transmitting from $S_2$ the sensing surface to a moisture detecting device that determines $S_1$ and $S_2$ a measure M of the moisture, said measure M being a function of $\sigma$, wherein the moisture detecting device comprises a first synchronous demodulator, wherein the method further comprises determining by the first synchronous demodulator the in-phase component $V_{IN}$ of $S_2$ relative to $S_1$, wherein M is a function of $V_{IN}$, and wherein $V_{IN}$ increases as $\sigma$ increases.

59. The method of claim 58, further comprising providing an electrically insulative enclosure that encloses the oscillator and the moisture detecting device, and wherein the sensing part comprises a probe located external to the enclosure.

60. The method of claim 58, further comprising:
providing an electrically insulative enclosure that encloses the oscillator and the moisture detecting device, wherein the sensing part comprises a sensing antenna, wherein the sensing antenna includes a transmitting element, a receiving element comprising the sensing surface, and a ground element, wherein the ground element is electrically connected to a ground potential within the enclosure, and wherein all electrically conductive surfaces within the enclosure are essentially capacitatively uncoupled to any electrical potential external to the enclosure; and
transmitting $S_1$ to the body by the transmitting element; and
receiving $S_2$ from the body by the receiving element.

61. The method of claim 60, wherein the sensing antenna comprises a two-conductor transmission line that includes the grounded conductor interposed between the transmitting element and the receiving element.

62. The method of claim 60, wherein the insulative material surrounds stator bars of a power generator.

63. The method of claim 62, further comprising holding the enclosure and its contents by a hand of a person.

64. The method of claim 60, further comprising moving the sensing surface into physical contact with the body by use of an electrically insulative handle mechanically connected to the enclosure.

65. The method of claim 60, wherein a flexible conductive interface electrically connects an element to the body, wherein the element is selected from the group consisting of the transmitting element, the receiving element, and the ground element.

66. The method of claim 65, wherein a constant-force assembly is coupled to the flexible conductive interface thereby causing the flexible conductive interface to exert an approximately constant force on the body, wherein the constant-force assembly includes a constant-force spring.

67. The method of claim 66, wherein a person comprises the body, and the method further comprises:
holding the enclosure and its contents at the band by a hand of a person; and
placing the sensing surface by the hand at a surface location on the skin of the person to determine M as a function of the surface location.

68. The method of claim 60, further comprising providing an electrically conductive band wrapped around the enclosure, wherein the conductive band includes the transmitting element.

69. The method of claim 58, further comprising using a second synchronous demodulator to determine from $S_1$ and $S_2$ the 90-degree out-of-phase component $V_{90}$ of $S_2$ relative to $S_1$, wherein $V_{90}$ is a measure of the degree of physical contact between the sensing surface and the body.

70. The method of claim 58, further comprising:
providing an internal switch within the first synchronous demodulator; and
switching $S_1$ and $S_2$ between a first and second switch setting of the internal switch, respectively, wherein the first switch setting enables a determination of $V_{IN}$, wherein the second switch setting enables a determination the 90-degree out-of-phase component $V_{90}$ of $S_2$ relative to $S_1$, and wherein $V_{90}$ is a measure of the degree of physical contact between the sensing surface and the body.

* * * * *